United States Patent
Schnaar et al.

(10) Patent No.: US 6,274,568 B1
(45) Date of Patent: Aug. 14, 2001

(54) COMPOUNDS FOR ALTERING CELL SURFACE SIALIC ACIDS AND METHODS OF USE THEREFOR

(76) Inventors: Ronald L. Schnaar, 9094 Goldamber Garth, Columbia, MD (US) 21045; Yoshitak Ichikawa, 7519 Stream Crossing Rd., Baltimore, MD (US) 21209; Brian E. Collins, 109C Dumbarton Rd., Baltimore, MD (US) 21212; Thomas J. Fralich, 3501 St. Paul St., Baltimore, MD (US) 21218

(*) Notice: Subject to any disclaimer, the term of this patent is extended or adjusted under 35 U.S.C. 154(b) by 0 days.

(21) Appl. No.: 09/370,074

(22) Filed: Aug. 6, 1999

Related U.S. Application Data

(60) Provisional application No. 60/095,493, filed on Aug. 6, 1998.

(51) Int. Cl.[7] .................................................. A61K 31/70
(52) U.S. Cl. ............................... 514/62; 514/8; 514/2; 536/53; 536/55.2; 435/7.1
(58) Field of Search ................ 514/62, 8, 2; 536/53, 536/55.2; 435/7.1

(56) References Cited

U.S. PATENT DOCUMENTS 5,225,352 * 7/1993 Zanetta et al. .................. 436/518
5,932,542 * 8/1999 Filbin ............................. 514/8
5,962,434 * 10/1999 Schnaar et al. ................ 514/54

OTHER PUBLICATIONS

Stehling et al.,"In vivo modulation of the acidic N–Glycans from rat liver dipeptidyl peptidase IV by N–Propanoyl–D–mannosamine", Biochem. Biophys. Res. Commun. (1999), 263(1). 76–80.*

Schumacher et al.,"Is the lectin binding pattern of human breast and colon cancer cells influenced by modulators of sialic acid metabolism", Histochem. Cell Biol. (1996), 106(6), 599–604.*

Kayser et al.,"Biosynthesis of a nonphysiological sialic acid in different rat organs, using N–Propanoyl–D–hexosamines as precursors", J. Biol. Chem., (1992), 267(24), 16934–8.*

* cited by examiner

*Primary Examiner*—Ralph Gitomer
*Assistant Examiner*—Devesh Khare
(74) *Attorney, Agent, or Firm*—Fish & Richardson P.C.

(57) ABSTRACT

The present invention is based on the identification of compounds in the form of biosynthetic precursors which can be used to modulate neuronal growth, inhibit cellular entry by pathogens and modulate immune responses. The invention further describes acylated mannosamines, and derivatives thereof, which can be used to alter the sialic acid substituents of sialoglycoconjugates.

19 Claims, 10 Drawing Sheets

COMPOUNDS FOR ALTERING CELL SURFACE SIALIC ACIDS AND METHODS OF USE THEREFOR

This application claims priority from U.S. Provisional Application Ser. No. 60/095,493 filed Aug. 6, 1998, the disclosure of which is incorporated herein by reference.

FIELD OF THE INVENTION

This invention relates to compounds for altering cell surface sialic acids and methods of using such compunds for modulating cellular lectin interactions with a glycoconjugate. The invention further relates to the use of such compounds for modulating cell growth.

BACKGROUND OF THE INVENTION

Lectins are proteins or glycoproteins that bind to sugar residues present in a glycoconjugate. The biological functions of lectins are based primarily on their capacity to recognize and target particular glycoconjugates. Lectins are candidates for attachment and recognition at cellular membranes as the sugar portions of glycoproteins and glycolipids are exposed at the outer surface of the protein-lipid bilayers that constitute these membranes. Various phenomena of cell—cell recognition are attributed to lectin-sugar interactions including mitogenic stimulation, pathogen attachment to a cell surface and immunologic stimulation.

Myelin associated glycoprotein (MAG) (Mukhopadhyay, et al. *Neuron* 13:757, 1994; McKerracher, et al. *Neuron* 13:805, 1994) is a sialic acid binding lectin and a member of the "siglec" family of immunoglobulin-like lectins (Crocker et al, *Glycobiology,* 8, 1998; Kelm et al., *Eur.J-.Biochem.* 255:663, 1998). In the nervous system, MAG functions in the stabilization of the myelin sheath surrounding axons (Lassmann et al., *Glia* 19:104, 1997; Sheikh et al., *Proc. Natl. Acad. Sci. U.S.A.* 96:7532, 1999), and in the control of axon cytoarchitecture (Yin et al., *J. Neurosci.* 18:1953, 1998).

A feature of axons in the peripheral nerves of adult mammals is that after interruption, they are able to regenerate through the distal nerve stump to reconnect with their targets and re-establish function. The same is not true however in the central nervous system (CNS). Axons injured in the brain, optic nerve or spinal cord of adult mammals do not successfully regrow. This leads to an irreversible disruption of neuronal circuits and permanent neurologic disability.

An increasing number of molecules regulating the growth of neuronal processes are being identified. Of considerable interest is the finding that the nervous system contains molecules which function to inhibit or restrict axonal growth. MAG recognition of sialoglycoconjugate targets on the surface of neuronal cells has been implicated in MAG inhibition of nerve regeneration (e.g. spinal cord) following injury (McKerracher et al., *Neuron* 13, 805, 1994; Mukhopadhyay et al., *Neuron,* 12:757, 1994; Schnaar et al., *Ann. N.Y. Acad. Sci.* 845:92, 1998). Sialic acids, a substituent of sialoglycoconjugates, are prominent termini of mammalian glycoconjugates and are binding determinants for cell—cell recognition lectins. Binding of the sialic acid-dependent lectin, myelin-associated glycoprotein (MAG), to nerve cells is implicated in the inhibition of nerve regeneration after injury. Sialic acids differ from other mammalian monosaccharides in their complexity, bearing a carboxylic acid group, an N-acyl substituent, and an exocyclic glycerol side chain (Varki, *Glycobiology* 2:25, 1992; Schauer, *Adv. Carbohydr. Chem. Biochem.* 40:131, 1982). Variety in sialic acid linkages as well as N- and O-acyl substituents results in a large number of unique structural determinants. Cell—cell recognition proteins, as well as pathogens and toxins, take advantage of the structural diversity and cell surface disposition of sialic acids for highly specific recognition and binding (McEver, *Glycoconj. J.* 14:585, 1997; Varki, *FASEB J.* 11:248, 1997; Kelm et al., *Glycoconj.J.,* 13:913, 1996; Miller-Podraza et al., *Glycoconj.J.* 14:467, 1997).

N-acetylneuraminic acid (NeuAc), the predominant sialic acid in nature, is synthesized in vivo by a multi step pathway (Roseman, *Chem. Phys. Lipids,* 5:270, 1970) beginning with the conversion of N-acetylglucosamine to N-acetylmannosamine-6-phosphate by a bifunctional epimerase/kinase (Hinderlich et al., *J. Biol. Chem.,* 272:24313, 1997; Kundig et al., *J. Biol. Chem.* 241:5619, 1966). ManNAc-6-P is converted to NeuAc-9-P by condensation with phosphoenol pyruvate, and then to CMP-NeuAc which is the activated NeuAc donor for glycolipid and glycoprotein oligosaccharide biosynthesis (Watson et al., *J. Biol. Chem.* 241:5627, 1966; Kean and Roseman, *J. Biol. Chem.,* 241:5643, 1966). Hydroxylation of NeuAc (in the CMP-NeuAc form) by a specific hyroxylase converts NeuAc to N-glycolylneuraminic acid (NeuGc), a member of the sialic acid family which is rare (or absent) in humans, but is common in non-neural tissues of many other species (Kawano et al., *J. Biol. Chem.,* 270:16458, 1995; Chou et al., *Proc. Natl. Acad. Sci. U.S.A.* 95:11751, 1998). However, this pathway can be short-circuited by addition of unnatural N-acylmannosamines, including N-propanoyl-, N-butanoyl-, N-pentanoyl-, and N-levulinoylmannosamine, among others (Angelino et al., *Carbohydr. Res.,* 276:99, 1995; Yarema et al., *J. Biol. Chem.* 273:31168, 1998). These precursors are taken up, converted to the corresponding sialic acids, and expressed on cell surface glycoconjugates.

Recently, it was reported that certain sialoglycoconjugates bearing N-acetylneuraminic acid (NeuAc) but not N-glycolylneuraminic acid (NeuGc) support MAG binding (Collins et al., *J. Biol. Chem.* 272:1248, 1997). Given the sensitivity of MAG binding to changes in sialic acid substructure, it would be desirable to develop biosynthetic precursors which would result in modification of a large proportion of the nerve cell sialic acid, rendering the cells resistant to the growth inhibitory effects of MAG binding. Knowledge of such precursors would form a basis for developing drug therapies which interfere with MAG's inhibitory effects, thus enhancing regeneration of nerves. The present invention provides compounds to address these needs, and provides improved methods for treating nerve injury.

SUMMARY OF THE INVENTION

The present invention is based on the discovery of a novel compound associated with cell—cell and cell-molecule interactions. The invention provides novel compounds, and methods of using such compounds, for modulating a cell surface sialoglycoconjugate. The compounds of the invention can be used as biosynthetic precursors for altering the response of a cell to a lectin, a pathogenic microbe or an immune system cell. Thus, the present invention provides a means for modulating a cell surface sialoglycoconjugate such that its recognition by a molecule or cell is altered.

It is an object of the present invention to provide a compound effective in modulating a cell surface sialoglycoconjugate. In accordance with one aspect of the present invention, an acylated mannosamine compound is provided.

In accordance with another aspect of the invention a method for modulating lectin binding to a cell surface by contacting a cell with a acylated mannosamine is provided.

In another aspect, the invention provides a method for modulating neuronal cell growth by contacting the cell with a therapeutically effective amount of a composition containing a acylated mannosamine.

In yet another aspect, the invention provides a method for the treatment of a lectin-mediated cell disorder by administering to a subject a therapeutically effective amount of a compound containing an acylated N-mannosamine, or a pharmaceutical composition thereof.

In another aspect, the invention provides a method for ameliorating a neuronal-associated disorder in a subject by administering to the subject having such a disorder, a therapeutically effective amount of a composition containing a acylated mannosamine.

In accordance with another aspect of the invention, a method is provided for ameliorating a lectin-mediated cell disorder, in a subject having the disorder, by administering to the subject a therapeutically effective amount of a composition which modulates the activity of the lectin associated with the disorder.

In yet another aspect, the invention provides a method of identifying a compound which modulates lectin-mediated inhibition of neuronal cell growth by contacting a neuronal cell with the compound under conditions which allow the compound to be incorporated in a glycoconjugate on the cell membrane and contacting a cell so treated with a lectin and detecting the effect of the compound on neuronal cell growth.

In another aspect, the invention provides a pharmaceutical composition for treatment of a cell disorder, comprising administering a therapeutically effective amount of a acylated mannosamine, with a pharmaceutically acceptable carrier.

In another aspect, the invention provides a method of inhibiting a pathogenic infection in a tissue, comprising contacting the tissue with a composition containing a acylated mannosamine.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION

Figure 1:
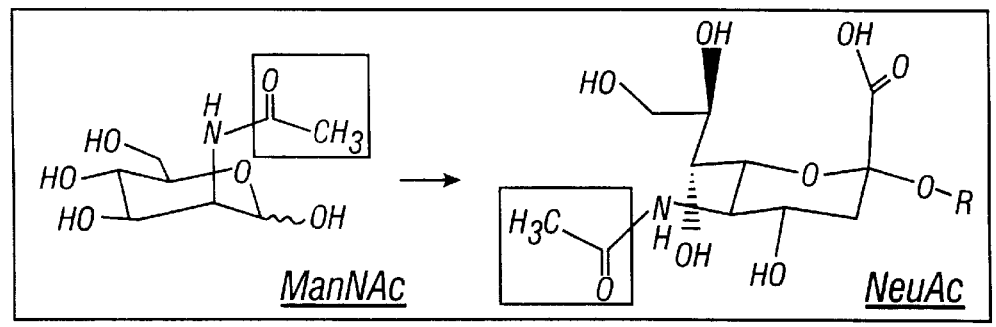
FIG. 1 shows N-acyl-D-mannosamine precursors and their corresponding sialic acids.
Figure 1:
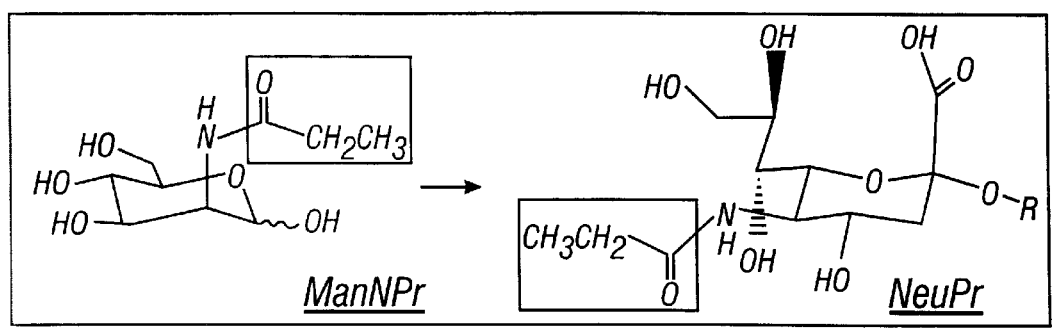
Figure 1:
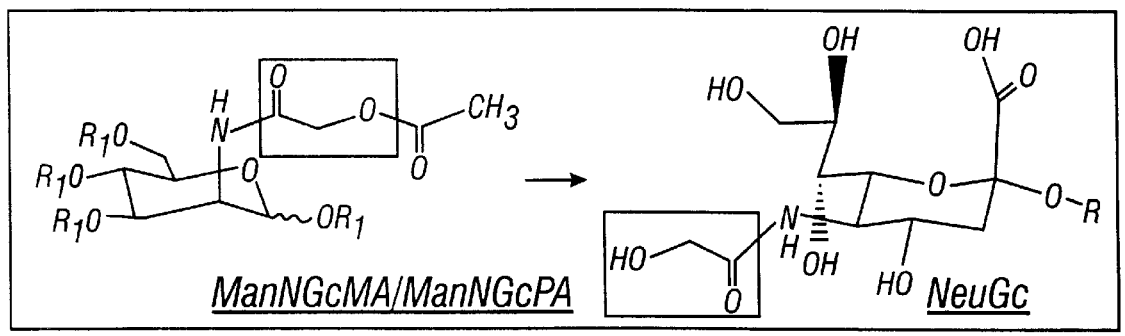

The present invention is based on the identification of compounds in the form of biosynthetic precursors which can be used to modulate neuronal growth, inhibit cellular entry by pathogens and modulate immune responses. The invention describes acylated mannosamines, and derivatives thereof, such as N-glycolylmannosamine peracylate, which can be used to alter the sialic acid substituents of sialoglycoconjugates. Such glycoconjugates are key binding determinants for cell—cell recognition lectins. Based on this discovery, it is an object of the invention to provide compounds, and pharmaceutical compositions thereof, which modulate lectin interactions with a target glycoconjugate. For example, compounds of the invention can be used to stimulate neuronal growth by inhibiting the neuronal inhibitory activity of the lectin known as myelin-associated glycoprotein (MAG).

Neuraminic acid is a diverse sugar that is a common termini of cell surface glycoconjugates. The predominant form of sialic acid, N-acetylneuraminic acid, is made in vivo from N-acetylmannosamine. Sialic acids are key determinants for binding many lectins, toxins, and pathogens. Sialic acids each have a carboxylic acid group, N-acyl group and an exocyclic glycerol chain, making them the most complex of mammalian monosaccharides. Variations in the N-acyl group and in O-acetylation provide a high degree of sialic acid structural diversity.

Although some sialic acid binding proteins are relatively indifferent to sialic acid fine structure, others bind with great specificity. Examples of sialic acid binding lectins are those of the siglec family, which are sensitive to modification of the carboxylic acid, the glycerol chain and/or the N-acyl moiety. Examples of such lectins are myelin-associated glycoprotein (MAG) and sialoadhesin. MAG and sialoadhesin bind NeuAc but not NeuGc on sialoglycoconjugate targets. Glycoconjugate modification has implications for modulating cell—cell interactions, particularly neural cell—cell interactions. In the present invention, novel compounds in the form of biosynthetic precursor derivatives were synthesized and used to modify lectin-targeted glycoconjugates.

In accordance with one aspect of the present invention, an acylated N-mannosamine compound is provided. In addition, the N-mannosamine can be peracylated. The N-mannosamine can be, for example, N-acetylmannosamine, N-propanoyl-mannosamine or N-glycolylmannosamine. The N-mannosamine can be, for example, N-glycolylmannosamine peracylate. Further, the N-mannosamine can be, for example, N-formylmannosamine peracylate. N-acetylneuraminic acid (NeuAc) can be O-acetylated or replaced by N-glycolylneuraminic acid (NeuGc).

In accordance with another aspect of the invention, a method for modulating lectin binding to a cell surface by contacting a cell with an acylated N-mannosamine is provided. In yet another embodiment, the invention provides a method of treating a subject having a lectin-mediated cell disorder, such that modulating the activity of the lectin would benefit a subject. The method includes administering to a subject having the disorder a therapeutically effective amount of an composition containing a compound of the invention which modulates the activity of a lectin, thereby treating the disorder. The term "modulate" refers to inhibition or suppression of lectin activity when the composition is administered. The term "therapeutically effective" means that amount of the composition is effective in reducing the symptoms of the lectin-mediated disorder.

In another aspect, the invention provides a method for modulating neuronal cell growth by contacting the cell with a therapeutically effective amount of a composition containing a acylated N-mannosamine. Neurogenesis, a biological process that includes the proliferation of neuronal cells, is defined as the generation and development of neurons. As used herein, the terms "neuronal tissue" or "neuronal cell" includes; motor neurons, which carry motor signals from the motor cortex within the central nervous system and from the central nervous system to muscles; sensory neurons, which carry signals from a wide range of sensory receptors in the periphery to the central nervous system; interneurons, which convey signals between neurons in the central nervous system; and neural tissue of the central nervous system (CNS).

Thus, in another embodiment, the invention provides a method for modulating neurogenesis in a tissue including contacting the tissue with a therapeutically effective amount of a composition containing a compound of the invention. It is envisioned that the method of the invention can be used to treat tissue damage in a subject after the tissue has been injured. The treatment can involve administering to the subject an effective amount of a composition containing a compound of the invention so as to contact the damaged tissue, thereby promoting neurogenesis in a tissue. Such regeneration would include, for example, axon outgrowth in damaged tissue.

Substances which modulate neuronal growth, including the biosynthetic precursors of the invention, may be useful in regulating neurite outgrowth in vivo and may form the basis for a strategy to enhance or inhibit neurite growth/axonal regeneration in the mammalian CNS. For example, the substances may be used to enhance (1) axonal regrowth in the CNS following traumatic CNS lesions; (2) formation of neuronal connections in neural transplantation therapies; and (3) the ability of surviving neurons to form new connections and thereby take over some of the functions of neurons lost in CNS neurodegenerative diseases such as Alzheimer's and Parkinson's Disease. Accordingly, the compounds identified herein may be used to stimulate or inhibit neuronal regeneration associated with conditions involving nerve damage resulting from nerve compression, nerve crush, nerve stretch or incomplete nerve transsection, contusion, nerve hemisection, or degenerative disorders of the central nervous system, for example Alzheimer's disease, Parkinson's disease, Huntington's disease, demyelinating diseases, progressive spinal amyotrophy, trauma and ischernia resulting from stroke, and tumors of nerve tissue, epilepsy, glaucoma, and neurofibromatosis.

Compounds of the invention, and derivatives thereof, possess significant therapeutic applications in promoting functional recovery from neuronal-associated disorders such as toxic, traumatic, ischemic, degenerative or inherited lesions to the peripheral or central nervous system. Furthermore, such compounds stimulate the growth of neuronal cells. As used herein, the term "growth" includes regrowth and outgrowth of neuronal cells. As used herein, the term "neuronal cell" encompasses cells of the nervous system including neurites. Thus, in another aspect of the present invention, there is provided a method of stimulating neurite outgrowth in differentiated or undifferentiated neuronal cells by administering to the neuronal cells an effective amount of a compound of the invention.

The method of the invention is useful in regenerating damaged neuronal tissue. For example, a method of the invention can be used to promote regeneration of tissue damaged as a result of a neuronal-associated disorder such as neuroma, nerve compression, nerve crush, nerve stretch or incomplete nerve transsection; mononeuropathy or polyneuropathy. As used herein, the term "regeneration" includes stimulating growth, regrowth or outgrowth of a neuronal tissue. A method of the invention also can be used to repair damage resulting from a disorder such as dorsal root ganglion compression; inflammation of the spinal cord; contusion, tumor or hemisection of the spinal cord; tumors of the brainstem, thalamus or cortex; or trauma to the brainstem, thalamus or cortex. As used herein, the term "disorder" means any trauma, injury, disease or condition resulting in resulting in neuronal tissue in need of regeneration.

The method of the invention can be particularly useful when a whole nerve is severely damaged or transsected, as in, for example, amputation, nerve transsection, nerve compression (entrapment neuropathies, tumors), nerve crush, stretch or incomplete transsection (trauma), spinal cord contusion, spinal cord hemisection or other trauma. Nerve compression can be abrupt, as in the case of traumatic nerve crush, or can be prolonged and moderate, secondary to tumor growth or scar formation in the proximity of a major nerve bundle. Compression neuropathy can occur as a result of changes in blood flow to a nerve, causing severe ischemia and consequent nerve injury.

A cell derived from the central nervous system can be particularly useful for transplantation to the central nervous system since the survival of such a cell is enhanced within its natural environment. A neuronal precursor cell is particularly useful in the method of the invention since a neuronal precursor cell can be grown in culture, treated with a compound of the present invention and introduced into an individual, where it is integrated. A cell so treated would not be susceptable to the inhibitory activity of endogenous lectins, such as MAG.

In yet another aspect, the invention provides method for the treatment of a lectin-mediated cellular adhesion disorder by administering to a subject a therapeutically effective amount of a compound of containing a acylated N-mannosamine, or a pharmaceutical composition thereof.

In accordance with another aspect of the invention, a method is provided for ameliorating a lectin-mediated cell proliferative disorder in a subject having the disorder by administering to the subject a therapeutically effective amount of a composition which modulates the activity of the lectin associated with the disorder.

As used herein, a "therapeutically effective amount" of a composition containing a compound, such as an acylated mannosamine or derivative thereof, for use in tissue repair is defined as that amount that is effective in promoting tissue regeneration. For example, a therapeutically effective amount of an acylated mannosamine refers to an amount sufficient to effectively induce axonal outgrowth so that regeneration of neurological tissue and neuronal connections are enhanced. Diseases, disorders or ailments modulated by acylated N-mannosamne include tissue repair, such as nerve tissue repair subsequent to traumatic injuries or conditions including arthritis, osteoporosis and other skeletal disorders, and burns. Because these problems are due to a poor growth response of neuronal tissue, fibroblasts, stem cells, chondrocytes, osteoblasts or fibroblasts at the site of injury, the addition of an active biologic compound that stimulates or induces growth of these cells is beneficial. The term "induce" or "induction" as used herein, refers to the activation, stimulation, enhancement, initiation and or maintenance of the cellular mechanisms or processes necessary for the formation of any of the tissue repair process or development as described herein.

In another aspect, the invention is useful for revitalizing neuronal tissue resulting from injuries due to surgical procedures, irradiation, laceration, toxic chemicals, viral infection, bacterial infection, burns or neuronal-associated disorders such as Parkinson's disease, Huntington's disease, demyelinating diseases, progressive spinal amyotrophy, trauma and ischemia resulting from stroke, and tumors of nerve tissue, epilepsy, glaucoma, and neurofibromatosis. For example, a compound of the invention can be included in a controlled release matrix which can be positioned in proximity to damaged tissue thereby promoting regeneration of such tissue. The term "controlled release matrix" means any composition which allows the slow release of a bioactive substance which is mixed or admixed therein. The matrix can be a solid composition, a porous material, or a semi-solid, gel or liquid suspension containing bioactive substances. The term "bioactive material" means any composition that will modulate tissue repair when used in accordance with the method of the present invention. The bioactive materials/matrix can be introduced by means of injection, surgery, catheters or any other means suitable for modulating tissue repair.

It is envisioned that the method of the invention can be used to aid wound repair in general, and neuronal tissue in particular, in guided tissue regeneration (GTR) procedures. Such procedures are currently used by those skilled in the medical arts to accelerate tissue regeneration following invasive surgical procedures. Typically, nonresorbable or bioabsorbable membranes are used to accelerate tissue regeneration by promoting the repopulation of the damaged area with cells which form the architectural and structural matrix of the tissue, including neuronal tissue. For example, the method of the invention can be used in aiding neuronal tissue regeneration in a human or lower animal by placing a composition containing a bioresorbable polymer, leachable solvent, and a compound of the invention at a site in need of neuronal tissue regeneration in a human or other mammal such that the composition is effective for aiding tissue regeneration by releasing a therapeutically-effective amount of the compound at the site.

In another aspect, the invention can be useful for the purposes of promoting tissue growth during the process of tissue engineering. As used herein, "tissue engineering" is defined as the creation, design, and fabrication of biological prosthetic devices, in combination with synthetic or natural materials, for the augmentation or replacement of body tissues and organs. Thus, the present method can be used to augment the design and growth of human tissues outside the body for later implantation in the repair or replacement of diseased tissues. For example, a compound of the invention may be useful in promoting the growth of nerve tissue graft replacements.

In another aspect of tissue engineering, a compound of the present invention can be included in cell-containing or cell-free devices which induce the regeneration of functional tissues when implanted at a site which requires regeneration. As previously discussed, biomaterial-guided tissue regeneration can be used to promote nerve regrowth. Thus, a compound of the invention can be used to promote the growth of reconstituted tissues assembled into three-dimensional configurations at the site of a damaged tissue or other tissue in need of such repair.

In another aspect of tissue engineering, a compound of the invention can be included in external or internal devices containing human tissues designed to replace the function of diseased internal tissues. This approach involves isolating cells from the body, placing them on or within structural matrices, and implanting the new system inside the body or using the system outside the body. The method of the invention can be included in such matrices to promote the growth of tissues contained in the matrices. For example, a compound of the invention can be included in a cell-lined graft to promote the growth of cells contained in the graft.

In another embodiment, the invention provides a method for ameliorating a lectin-mediated disorder, including treating a subject having the disorder, at the site of the disorder, with a composition which regulates the effect of the lectin on a cell. A "lectin-mediated cell disorder" is any disorder resulting from, at least in part, the presence of a lectin in a particular environment which adversely effects the growth, regrowth or outgrowth of a cell, for example, MAG inhibition of neuronal outgrowth. The term "ameliorate" denotes a lessening of the detrimental effect of the disorder-inducing response in the subject receiving therapy. Thus, the method includes promoting tissue regeneration in tissue normally refractory to such regeneration. For example, the method of the invention is useful for promoting regeneration of tissue of the central nervous system which contains cells normally growth inhibited. For example, myelin-associated glycoprotein (MAG) is a lectin which has been implicated in the undergrowth of neuronal tissue by interacting with a target glycoconjugate on the surface of a neuronal cell and inhibiting axon outgrowth. Methods of the present invention can be used to alter a target glycoconjugate on a cell surface such that a growth inhibiting lectin no longer interacts with the target glycocojugate. Thus, the method of the invention can be used to inhibit the growth inhibiting activity of a lectin, such as MAG.

The term "cell proliferative disorder", as used herein, refers to a condition characterized by abnormal cell growth. The condition can include both hypertrophic (the continual multiplication of cells resulting in an overgrowth of a cell population within a tissue) and hypotrophic (a lack or deficiency of cells within a tissue) cell growth or an excessive influx or migration of cells into an area of a body. The cell populations are not necessarily transformed, tumorigenic or malignant cells, but also can include normal cells.

Screening Method for Acylated Mannosamine Biosynthetic Precursors

The invention further provides a method for identifying biosynthetic precursors which modulate the ability of a lectin, such as, for example, MAG, to interact with its sialylated ligand. The method includes: a) incubating components comprising the precursor under conditions sufficient to allow the precursor, or derivatives thereof, to be incorporated on a membrane surface, and contacting the precursor or its derivative with a lectin, thereby allowing the components to interact; and b) determining the effect of the precursor on the lectin's ability to interact with the sialylated ligand before and after incubating in the presence of the precursor. Thus, in another aspect, the invention provides a method of identifying a compound which modulates lectin-mediated inhibition of neuronal cell growth by contacting a neuronal cell with the compound under conditions which allow the compound to be incorporated in a glycoconjugate on the cell membrane, contacting a cell so treated with a lectin and detecting the effect of the compound on neuronal cell growth.

For example, the invention provides a method for identifying a compound which alters a cell surface glycoconjugate thereby inhibiting myelin-associated glycoprotein (MAG) inhibition of axonal growth. Such compounds are capable of stimulating axonal outgrowth when brought in contact with nerve cells by virtue of their ability to inhibit MAG interaction with a cell surface. The claimed method comprises contacting the compound with a cell under conditions which allow the compound to enter the cell and alter a cell surface glycoconjugate. The method further comprises contacting a cell so treated with MAG under conditions which allow MAG and the cell comprising an altered glycoconjugate to interact. The method detects the binding or inhibition MAG interaction with the cell, as well as characterizing the affinity between the compound and MAG, and the compounds ability to inhibit (i.e. diminish) MAG inhibitory activity.

Compounds, such as biosynthetic precursors, can be screened using the claimed method to identify those which modulate lectin, such as, for example, MAG, binding. These compounds which are present on glycolipids, particularly gangliosides, can be screened for their effect on lectin binding to the glycolipid. Gangliosides represent a large and varied family of sialic acid containing cell surface glycosphingolipids (C. L. M. Stults, et al., *Methods Enzmol.* 167 (1989); R. K. Yu, M. Saito, in *Neurobiology of Glycoconjugates,* R. U. Margolis and R. K. Margolis, Eds. (Plenum Press, New York, 1989).

Contacting includes in solution and in solid phase, or in a cell. The precursor may optionally be a combinatorial library for screening a plurality of biosynthetic precursors. Precursors identified in the method of the invention can be further evaluated, detected and the like, either in solution or after binding to a solid support, by any method usually applied to the detection of a specific interaction.

As previously noted, included in the screening method of the invention are combinatorial chemistry methods for identifying biosynthetic precursors which modulate the ability of a lectin to interact with its sialylated ligand. It is envisioned that the method of the invention can be used to identify precursors that modulate the action of a lectin. Areas of investigation for combinatorial chemistry are the development of therapeutic treatments. Drug screening identifies agents or compounds that provide a replacement, enhancement or regulation of a sialylated ligand function in affected cells. Of particular interest are screening assays for compounds that have a low toxicity for human cells. The sialylated ligand may also be used for determination of three-dimensional crystal structure.

Candidate compounds encompass any biosynthetic precursor useful for altering a cell surface glycoconjugate. Candidate compounds are obtained from a wide variety of sources including libraries of synthetic or natural compounds. For example, numerous means are available for random and directed synthesis of a wide variety of organic compounds and biomolecules. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification or amidification to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein—protein binding and/or reduce non-specific or background interactions. Reagents that improve the efficiency of the assay, such as protease inhibitors, nuclease inhibitors or anti-microbial agents may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

The claimed method is operable for contacting compounds with MAG under soluble or surface-bound conditions. Thus, both the candidate test compound and MAG can be screened for binding between both moieties when both are in soluble phase. Under such conditions, detection of the binding between MAG and the test compound is facilitated by the use of detectably labeled compounds, or by the use of detectably labeled MAG. Preparation of detectably labeled compounds, and in particular, detectably labeled MAG or other proteins; and detectably labeled glycosides or gangliosides, involves procedures well known in the art (Current Protocols in Molecular Biology, ed. Ausubel, F. M. et al., publ., John Wiley & Sons, Inc., 1994—Section 10.18 for proteins; Section 17 for glycolipid compounds). Accordingly, MAG or candidate compounds can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to MAG, and test compounds, or will be able to ascertain such, using routine experimentation.

The compounds identified herein may be incorporated into a pharmaceutical composition containing the substance, alone or together with other active substances. Thus, in another aspect, the invention provides a pharmaceutical composition for treatment of a cell disorder, comprising a therapeutically effective amount of a acylated mannosamine, with a pharmaceutically acceptable carrier. Such pharmaceutical compositions can be for oral, topical, rectal, parenteral, local, inhalant or intracerebral use. They are therefore in solid or semisolid form, for example pills, tablets, creams, gelatin capsules, capsules, suppositories, soft gelatin capsules, gels, membranes, tubeless. The methods described by Penn et al, Lancet 335(8691):738–747, 1990 for intrathecally delivering substances into the CNS may be particularly useful for administering the pharmaceutical compositions of the invention.

Compounds in the form of biosynthetic precursors according to the present invention can be administered to a subject in any acceptable manner including orally, by injection, using an implant, nasally and the like. Oral administration includes administering a compound of the present invention, such as a biosynthetic precursor, in tablets, suspension, implants, solutions, emulsions, capsules, powders, syrups, water composition, and the like. Nasal administration includes administering the composition of the present invention in sprays, solutions and the like. Injections and implants are preferred because they permit precise control of the timing and dosage levels useful for administration, with injections being most preferred.

Biosynthetic precursors of the invention may be directly introduced into cells or tissues in vivo using physical techniques such as microinjection and electroporation or chemical methods such as coprecipitation and incorporation. Such molecules may also be delivered in the form of an aerosol or by lavage. The compound of the invention may also be applied extracellularly such as by direct injection into cells. Freed et al., New Eng. J. Med. 327(22):1549–1555, 1992, describe a method for injecting fetal cells into brains of Parkinson's patients. The methods described by Pace et al, Lancet 335(8691):738–747 for intrathecally delivering substances into the CNS may also be useful for administering pharmaceutical compositions containing biosynthetic precursor molecules of the invention.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

The invention also includes a pharmaceutical composition for therapy comprising an effective amount of a biosynthetic precursor of the invention or combination thereof, and a physiologically acceptable excipient or carrier. The pharmaceutical compositions include, albeit not exclusively, the active compound or substance in association with one or more pharmaceutically acceptable vehicles or diluents, and contained in buffered solutions with a suitable pH and iso-osmotic with the physiological fluids, The pharmaceutical compositions may additionally contain other agents such as neurotrophic factors, in particular NGF, BDNF, CNTF, T-3 and FGF. Pharmaceutical compositions containing a biosynthetic precursor of the invention can be administered parenterally by injection or by gradual perfusion over time. Administration may be intravenously, intraperitoneally, intramuscularly, subcutaneously, intra-cavity, or transdermally.

Physiologically acceptable and pharmaceutically acceptable excipients and carriers are well known to those of skill in the art. By "physiologically or pharmaceutically acceptable carrier" as used herein is meant any substantially non-toxic carrier for administration in which a biosynthetic precursor of the invention will remain stable and bioavailable when used. For example, the biosynthetic precursor of the invention can be dissolved in a liquid, dispersed or emulsified in a medium in a conventional manner to form a liquid preparation or is mixed with a semi-solid (gel) or solid carrier to form a paste, ointment, cream, lotion or the like.

Suitable carriers include water, petroleum jelly (vaseline), petrolatum, mineral oil, vegetable oil, animal oil, organic and inorganic waxes, such as microcrystalline, paraffin and ozocerite wax, natural polymers, such as xanthanes, gelatin, cellulose, or gum arabic, synthetic polymers, such as discussed below, alcohols, polyols, water and the like. Preferably, because of its non-toxic properties, the carrier is a water miscible carrier composition that is substantially miscible in water. Such water miscible carrier composition can include those made with one or more ingredients set forth above but can also include sustained or delayed release carrier, including water containing, water dispersable or water soluble compositions, such as liposomes, microsponges, microspheres or microcapsules, aqueous base ointments, water-in-oil or oil-in-water emulsions or gels.

The carrier can comprise a sustained release or delayed release carrier. The carrier is any material capable of sustained or delayed release of the biosynthetic precursor to provide a more efficient administration resulting in one or more of less frequent and/or decreased dosage of the precursor molecule, ease of handling, and extended or delayed effects. The carrier is capable of releasing the precursor when exposed to the environment of the area for diagnosis or treatment or by diffusing or by release dependent on the degree of loading of the precursor to the carrier in order to obtain release. Non-limiting examples of such carriers include liposomes, microsponges, microspheres, gene-activated matrices, as described above, or microcapsules of natural and synthetic polymers and the like. Examples of suitable carriers for sustained or delayed release in a moist environment include gelatin, gum arabic, xanthane polymers; by degree of loading include lignin polymers and the like; by oily, fatty or waxy environment include thermoplastic or flexible thermoset resin or elastomer including thermoplastic resins such as polyvinyl halides, polyvinyl esters, polyvinylidene halides and halogenated polyolefins, elastomers such as brasiliensis, polydienes, and halogenated natural and synthetic rubbers, and flexible thermoset resins such as polyurethanes, epoxy resins and the like.

The effective amount of a biosynthetic precursor of the invention used for therapy or diagnosis of course can vary depending on one or more of factors such as the age and weight of the patient, the type of formulation and carrier ingredients, frequency of use, the type of therapy or diagnosis preformed and the like. It is a simple matter for those of skill in the art to determine the precise amounts to use taking into consideration these factors and the present specification.

Inhibition of Pathogen Attachment by Acylated Mannosamine Compounds

The infection of a host cell by a pathogen, such as a virus, a bacterium or a protozoan, proceeds via initial attachment of the pathogen to the host cell surface. This process is mediated by relatively weak attractive interactions between adhesion molecules on the surfaces of the pathogen and the host cell. In general, pathogen-host cell attachment is the product of a multiplicity of such interactions, via what has been referred to as the polyvalent effect. For example, attachment of the influenza A virus to mammalian epithelial cells results from interaction of terminal N-acetylneuraminic acid groups of glycolipids and glycoproteins on the host cell surface with the attachment glycoprotein hemagglutinin on the viral surface. The growing problem of bacterial resistance to conventional antibiotics and the paucity of effective antiviral agents both point to the need for new approaches to the treatment of microbial infections. The attachment step between the pathogen and the host cell is an attractive target for such a treatment, and much activity has focused on the development of N-acetylneuraminic acid-containing compounds capable of binding to viral hemagglutinin, thus inhibiting viral attachment to host cells. Studies have demonstrated that polyvalent compounds, such as polymers bearing pendant N-acetylneuraminic acid groups, bind influenza virus with association constants which are several orders of magnitude higher than those of monomeric N-acetylneuraminic acid derivatives. To date, no polyvalent N-acetylneuraminic acid containing compounds are in clinical use for treatment or prevention of influenza.

There is a need for inhibitors of pathogenic attachment to mammalian cells which have have a broad spectrum of activity. Thus, in another aspect, the invention provides a method of inhibiting a pathogenic infection in a tissue, comprising contacting the tissue with a composition containing an acylated mannosamine resulting in the alteration of a cell surface glycoconjugate, thereby inhibiting pathogenic attachment.

The term "pathogenic infection", as used herein, refers to the infection of a host organism, such as a mammal, by a pathogenic microbe or microbes, such as bacteria, viruses or protozoa. Pathogenic infections which can be treated or prevented by the method of the present invention include bacterial infections, such as infection by Streptococcus, including *Streptococcus mutans, Streptococcus salivarius,* and *Streptococcus sanguis;* Salmonella, Campylobacter, including *Campylobacter sputum;* Antinomyces, including *Actinomyces naeslundii* and *Actinomyces viscosus, Escherichia coli, Clostridium difficile,* Staphylococcus, including *S. aureus;* Shigella, Pseudomonas, including *P. aeruginosa; Eikenella corrodens, Actinobacillus actinomycetemcomitans, Bacteroides gingivalis,* Capnocytophaga, including *Capnocytophaga gingivalis; Wolinell recta, Bacteriodes intermedius,* Mycoplasma, including *Mycoplasma salivarium,* Treponema, including *Treponema denticola; Peptostreptococcus micros,* Vibrio, Bacteriodesforsythus, Fusobacteria, including *Fusobacterium nucleatum; Selenomonas sputigena,* Bacteriodesfragilis, *Enterobacter cloacae* and Pneumocystis. Also included are protozoal infections, such as infection by *Cryptosporidium parvum,* Cyclospora and *Giardia lamblia;* ameobic infections, such as infection by *Entameoba histolytica* or Acanthameoba; fungal infections, such as infections by *Candida albicans* and *Aspergillus fumigatus,* and parasitic infections, such as infections by *A. castellani* and *Trichinella spiralis.* Viral infections for which the present compounds and methods are suitable include infections by rotavirus, influenza virus and Norwalk virus. The method is useful for treating infections of various tissues and organs of the body, but is particularly useful for infections of the skin and gastrointestinal tract.

Immune Modulation by Acylated Mannosamine Compounds

A macrophage (i.e., mononuclear phagocyte) is a phagocytic cell of the myeloid lineage found in all organs and connective tissue. Macrophages are antigen-presenting cells which phagocytize and kill bacteria, viruses, and foreign particles, and processes them for presentation to T cells. Macrophages are also involved in clearing antigen-antibody complexes from the tissues. Migration of macrophages from blood vessels in to distressed or damaged tissues is crucial to the initiation of normal disease fighting inflammatory responses. Cytokines produced by activated helper T cells stimulate phagocytosis and other macrophage functions.

Myelin-associated glycoprotein (MAG) and sialoadhesin (Sn) bind to sialylated glycoconjugates on cell surfaces and are thought to be involved in cell—cell interactions. Sialoadhesin is a macrophage-restricted transmembrane glycoprotein that mediates cell—cell interactions through recognition of glycoconjugates and belongs to the Ig superfamily of receptor-like molecules. The sialoadhesin family are able to mediate sialic acid-dependent binding with distinct specificities for both the type of sialic acid and its linkage to subterminal sugars. Recent studies suggest that sialoadhesin may contribute to a range of macrophage functions, both under normal conditions as well as during inflammatory reactions.

Thus, in another embodiment, the invention provides a method of modulating macrophage activity, including contacting the macrophage with an effective amount of a compound of the invention. Thus, compounds of the invention are useful for modulating macrophage activity at the site of damaged and/or infected tissues for the purpose of preventing or ameliorating disease states associated with viral or bacterial infections. Previously disclosed methods for applying compositions containing a compound of the invention to a site in need of such treatment can be used to promote the prevention or treatment of an infection.

Macrophage recruitment is also involved in the onset and progression of debilitating and life-threatening inflammatory and autoimmune diseases. The pathology of these diseases results from the attack of the body's immune system defenses on normal tissues. Thus, in another aspect of the invention, a composition containing a compound of the invention which modulates the activity of a macrophage can be used to prevent or ameliorate a disease state associated with inflammatory and autoimmune diseases. These disease include, but are not limited to, rheumatoid arthritis, psoriasis, contact dermatitis, inflammatory bowel disease, multiple sclerosis, atherosclerosis, sarcoidosis, idiopathic pulmonary fibrosis, dermatomyosititis, hepatitis, diabetes, allograft rejection and graft-vs-host disease.

Without further elaboration, it is believed that one skilled in the art can, using the preceding description, utilize the present invention to its fullest extent. The following examples are to be considered illustrative and thus are not limiting of the remainder of the disclosure in any way whatsoever.

EXAMPLE 1

Materials and Methods

Mannosamine Precursors and Sialic Acid Derivatives:

The chemical structures for D-mannosamine precursors used in the present invention and their corresponding sialic acid derivatives are shown in FIG. 1. N-acetylmannosamine (ManNAc) (FIG. 1, top panel) and N-propanoylmannosamine (ManNPr) (FIG. 1, center panel) are converted intracellularly to N-acetylneuraminic acid (NeuAc) and N-propanoylneuraminic acid (NeuPr) respectively. N-glycolyl-mannosamine (ManNGc) (FIG. 1, bottom panel) was synthesized as N-glycolyl-mannosamine monoacetate (ManNGcMA, $R_1$=H) or N-glycolylmannosamine pentaacetate (ManNGcPA, $R_1$=—C(=O)$CH_3$). Each is presumably deacetylated intracellularly by non-specific esterases, forming ManNGc, which is then converted to N-glycolylneuraminic acid (NeuGc). Cellular sialic acids are found as the free saccharide (R=H), as the activated sugar donor (R=CMP), or in glycoconjugates (R=any of the oligosaccharide structures to which sialic acid is attached). D-Mannosamine-HCl, ManNAc, NeuAc, and NeuGc were purchased from Sigma Chem. Co. (St. Louis).

Figure 2:
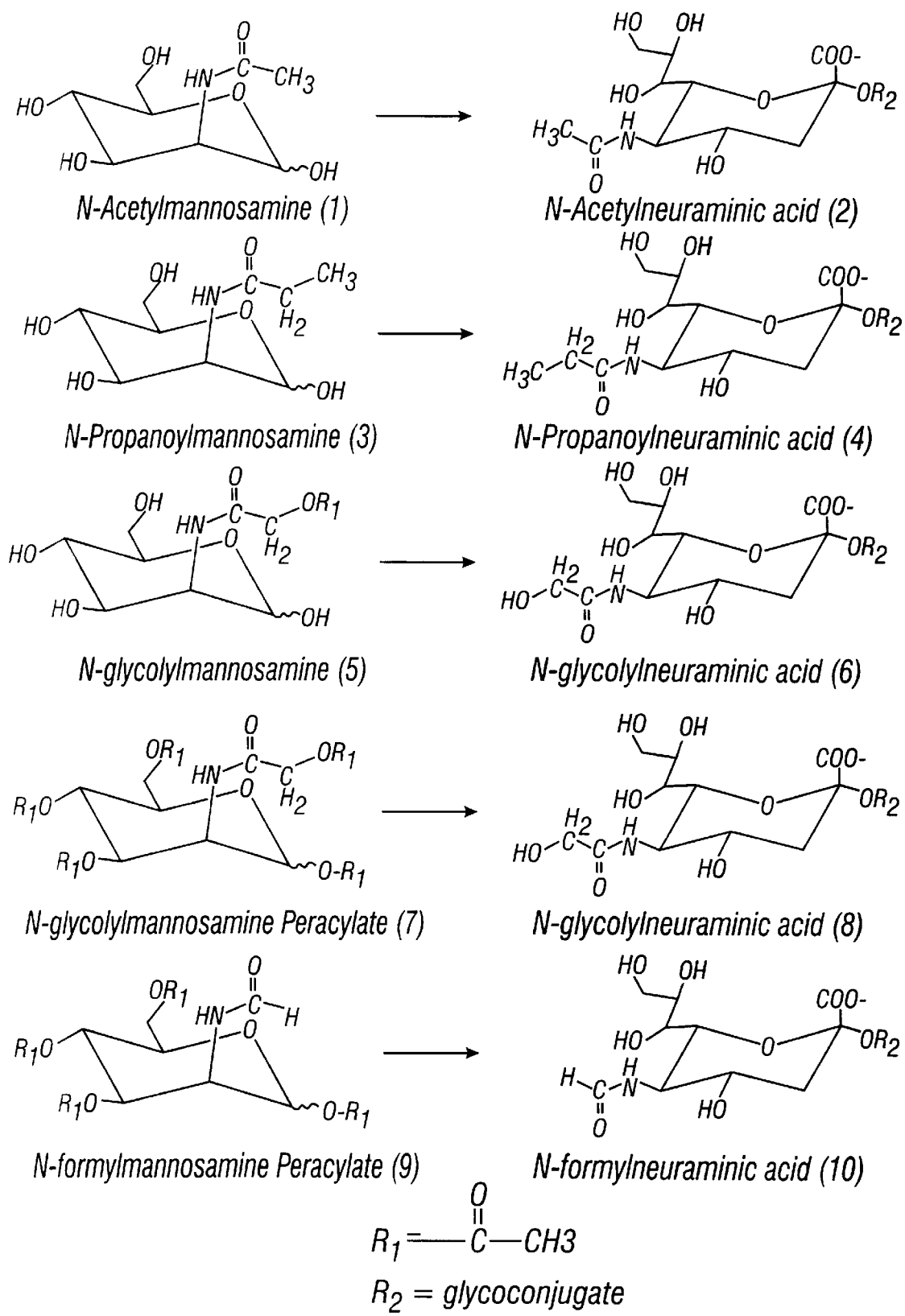
FIG. 2 shows the chemical structures for D-mannosamine precursors used in the present invention and their corresponding sialic acid derivatives.

Additional chemical structures for D-mannosamine precursors used in the present invention and their corresponding sialic acid derivatives are shown in FIG. 2 and include: (1) N-acetylmannosamine (ManNAc); (2) N-acetylneuraminic acid (NeuAc); (3) N-propanoylmannosamine (ManNPr); (4) N-propanoylneuraminic acid (NeuPr); (5) N-glycolylmannosamine (ManNGc); (6) N-glycolylneuraminic acid (NeuGc); (7) peracetylated ManNGc derivative; (8) N-glycolylneuraminic acid (NeuGc); (9) N-formylmannosamine (ManNFr); (10) N-formylneuraminic acid (NeuFr).

N-Glycolylmannosamine monoacetate (ManNGcMA, FIG. 1) was synthesized using the method of Kuboki et al. (Kuboki et al., Tetrahedron 53:2387, 1997). Briefly, D-Mannosamine-HCl (1 g) and sodium bicarbonate (7.5 g) were added to 40 ml water. After chilling the mixture on ice, 2.6 ml of acetoxyacetyl chloride (Aldrich Chem. Co., Milwaukee) were added dropwise and the reaction stirred for 3 h on ice. Formation of the desired product was confirmed by silica gel thin layer chromatography, using ethyl acetate-acetic acid-water (3:2:1) as developing solvent, ninhydrin to detect unreacted starting material, and orcinol-sulfuric acid reagent (Schnaar and Needham, *Methods Enzymol.*, 230:371, 1994) to detect sugars (product $R_f$=0.63). After filtering through Celite, the filtrate was neutralized with 2 M HCl and concentrated. The product was purified by silica gel column chromatography using ethyl acetate-isopropanol-water (27:8:4) as the eluant. The product, whose identity was confirmed by $^1$H NMR, was dissolved in water and stored at −20° C. Product concentration was determined by quantitative high performance liquid chromatography on a Dionex Carbopac column with pulsed amperometric detection (Hardy et al., *Anal. Biochem.* 170:54, 1988) using ManNAc as a quantitative standard.

N-Glycolylmannosamine pentaacetate (ManNGcPA) was prepared by treating ManNGcMA (0.3 g) with acetic anhydride (2 ml) in pyridine (2 ml) for 1 h at ambient temperature. The reaction was monitored by silica gel thin layer chromatography, using toluene-ethanol (10:1) as the developing solvent and orcinol-sulfuric acid reagent to visualize sugars (product $R_f$=0.32). The reaction mixture was concentrated and the product purified by silica gel column chromatography using step-wise elution with toluene, toluene-ethanol (50:1), and toluene-ethanol (20:1) as the eluants. Fractions containing the desired product were evaporated, resuspended in DMSO and the concentration determined by quantitative high pressure liquid chromatography. The structure of the peracetylated compound was confirmed by $^1$H NMR, which revealed full O-acetylation and an α:β ratio of 2:1.

N-Propanoylmannosamine (ManNPr) was synthesized according to the method of Keppler et al. (*J.Biol.Chem.* 270:1308, 1995). D-Mannosamine-HCl (3 mmol), sodium methoxide (3.3 mmol), and propionic anhydride (3.6 mmol) in 300 ml of methanol were stirred for 2 h at 0° C. The desired product was isolated by silica gel column chromatography using ethyl acetate-methanol-water (5:2:1) as the eluant. Fractions were analyzed by thin layer chromatography using the same solvent for development and orcinol-sulfuric acid reagent for detection ($R_f$=0.59). Fractions containing product were combined, evaporated to dryness, the residue dissolved in water, and stored at −20° C. N-Propanoylneuraminic acid (NeuPr) standard was prepared enzymatically by reacting ManNPr with pyruvate using N-acetylneuraminic acid aldolase (Sigma).

ManNFr was synthesized using the method described by Ichikawa et al. (*Glycoconj. J.* 7:335, 1990). D-mannosamine HCl (1 g) was suspended in 10 mL methanol and 50% v/v AG1x8 (OH—) (10 mL; Biorad, Hercules, Calif.) was added to the solution. The mixture was allowed to react with end-over-end mixing for 1 hour at 37° C. and then filtered and evaporated to dryness. The formyl derivative was prepared by resuspending the product in 10 mL saturated sodium bicarbonate, then adding methyl formate (3 mL; Sigma). The reaction was carried out overnight at room temperature and the product was analyzed by TLC in ethyl acetate/acetic acid/water (3:2:1). The peracetylated compound was then prepared by reacting ManNFr from above with 10 mL acetic anhydride (Sigma) in 15 mL pyridine for 2 hours at room temperature. Saturated sodium bicarbonate was added, followed by extraction with 100 mL chloroform. The chloroform was then re-extracted and the combined aqueous phases were back-extracted with 50 mL chloroform. The combined chloroform fractions were analyzed by TLC in toluene/ethanol (10:1) and the product was purified by silica gel column chromatography as described for the peracetylated ManNGc derivative.

Cell Culture and Treatment with Sialic Acid Biosynthetic Precursors

NG108-15 cells were maintained in Dulbecco's modified Eagle's medium (high glucose formulation) containing 5% iron-enriched calf serum, 100 μM hypoxanthine, 16 μM thymidine, and 5 μM aminopterin. Jurkat cells were maintained in RPMI Medium 1640 (Gibco Life Technologies, Gaithersburg, Md.) supplemented with 10% fetal bovine serum. Both cell types were cultured at 37° C. in a humidified atmosphere of 90% air/10% $CO_2$. For treatment with sialic acid precursors, mannosamine derivatives were diluted into the appropriate medium and filter sterilized. The growth medium was then replaced and cells were cultured in the presence of the precursor for 24–144 h. In experiments testing ManNGcPA, all cells (control and experimental) were grown in the presence of 0.5% (v/v) DMSO, the carrier for ManNGcPA.

Sialic Acid Analysis:

Cells were harvested using hypertonic $Ca^{2+}$- and $Mg^{2+}$-free phosphate-buffered saline containing 1 mM EDTA, collected by centrifugation, and homogenized in ice-cold water using a Potter-Elvehjem glass/Teflon homogenizer. Methanol (2.6 volumes) was added, the suspension mixed and brought to ambient temperature, then chloroform (1.3 volumes, based on the original homogenate) was added and the suspension mixed vigorously. The suspension was centrifuged 30 min at 2,000×g. After collecting the supernatant, the pellet (containing precipitated proteins) was resuspended in water or concentrated ammonium hydroxide and a portion was used for protein assay (BCA, Pierce, Rockford, Ill.). The supernatant was partitioned by adjusting the chloroform-methanol-water ratio to 4:8:5.6 by addition of water, mixing thoroughly, and centrifuging as above. The upper phase was collected and a portion was subjected to reverse phase chromatography, using Sep-Pak C18 cartridges (Waters, Milford, Mass.), to isolate gangliosides (Schnaar, *Methods Enzymol.* 230:371, 1994).

To quantify and identify sialic acids, a portion of resolublized protein, organic/aqueous soluble pool, or reverse-phase purified gangliosides was evaporated to dryness in a 500-μl polypropylene tube and 20 μl of 0.1 M HCl/0.25 M NaCl was added. One Ampliwax bead (Perkin Elmer Corp, Foster City, Calif.) per reaction was added to block evaporation, and the sample hydrolyzed for 3 h at 80° C. Released sialic acids were analyzed by injecting an aliquot (1–10 μl) onto a Dionex high pressure liquid chromatography system (Dionex Corporation, Sunnyvale, Calif.) using a HPIC-AS6 column and a pulsed amperometric detector. Elution solutions were: A, 0.75 mM NaOH; B, 200 mM NaOH; and C, 400 mM sodium acetate in 50 mM NaOH. NeuAc and NeuPr were resolved by elution with 40% A, 50% B, 10% C for 15 min at 1 ml/min. NeuGc was resolved in separate injections using step gradient elution: 0–1.8 min, 18% A, 50% B, 32% C; 2–10 min, 40% B, 60% C. Sialic acids were identified by comparison of their elution time with those of standard NeuAc, NeuPr and NeuGc and were quantified in comparison to a standard curve of commercial NeuAc (for NeuAc and NeuPr) or NeuGc.

To confirm that the quantified peaks represented sialic acids, 10 μl of acid hydrolysates were treated with 1 μl of 1 M sodium phosphate (pH 7.2) and 10 μl of 0.1 M NaOH. Neutralized samples were incubated at 37° C. for 2 h with or without 0.9 U of N-acetylneuraminic acid aldolase (Sigma), 32 μM NADH and 0.1 μg lactate dehydrogenase. Sialic acid content in the ganglioside and glycoprotein fractions is expressed per mg of total cell protein. Precursor pool sialic acid (sialic acid plus CMP-sialic acid) was calculated by subtracting the ganglioside value from the organic/aqueous pool value, both expressed per mg of cell protein.

Figure 5:
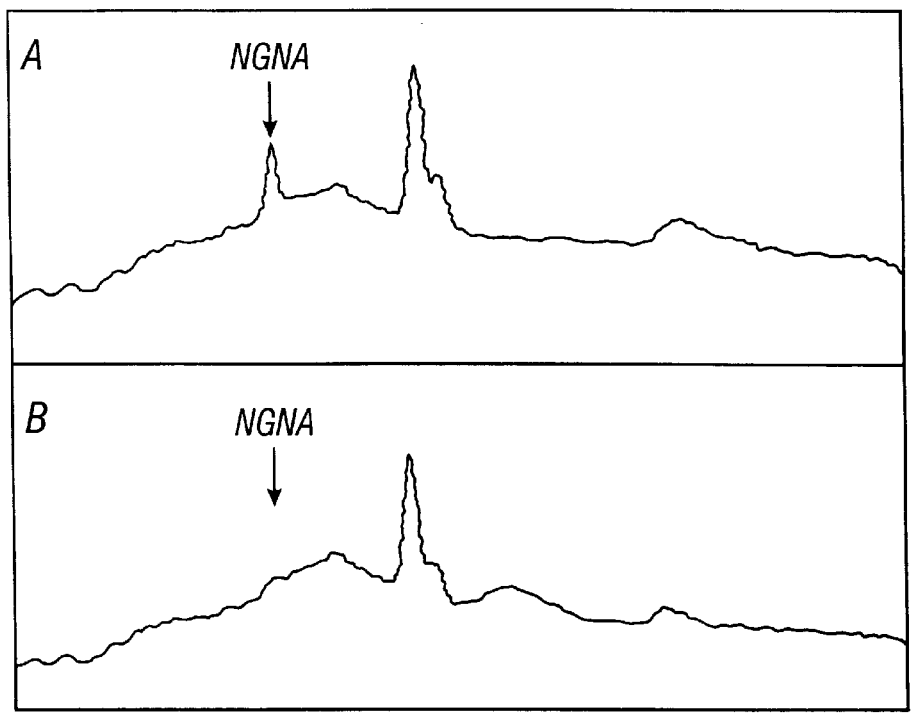
FIG. 5 is a graph showing aldolase elimination of NeuGc in sialic acid extract from ManNGc treated NG108-15 cells.

Aldolase Treatment:

Acid hydrolysates of intracellular and lipid associated sialic acid from 20 mM ManNGc treated NG108-15 cells were neutralized with 1/10 volume 1 M sodium phosphate (pH 7.2) and an equal volume of 0.1 M NaOH. The samples were then incubated at 37° C. for 2 hours in the presence or absence of 0.9 units N-acetylneuraminic acid aldolase (Sigma) with 32 μM NADH and 0.1 μg lactate dehydrogenase. The hydrolysates were neutralized with 1/10 volume 1 M sodium phosphate (pH 7.2) and an equal volume of 0.1 M NaOH. Aldolase and mock aldolase reactions were carried out in the absence (panel A) or presence (panel B) of N-acetylneuraminic acid aldolase (0.9 U) for 2 hours at 37° C. with 32 μM NADH and 0.1 μg lactate dehydrogenase. Loss of sialic acid following aldolase treatment was observed by HPLC (FIG. 5).

MAG Binding:

Flow cytometry was used to test binding of a soluble MAG-Fc chimera to precursor-treated and control NG108-15 cells. A chimeric protein consisting of the entire extracellular domain of MAG fused via a three amino acid bridge (TGK) to the human Fc domain was produced using the "pIgPlus" vector (Novagen, Madison, Wis.). A PCR fragment coding for the extracellular domain of MAG was prepared using MAG in pCDM8 as template (Yang et al., 1996a), the T7 5' primer TAATACGACTCACTATAGG (SEQ ID NO:1) and GATCGGATCCTTACCTGTTTTG-GCCCACATCAGTCGGTGTGC (SEQ ID NO:2) as the 3' primer. The fragment was cut with BamHI and HindIII and directionally cloned into the pIgPlus vector. The resulting construct was sequenced to confirm its identity, transfected into COS cells, and the resulting MAG-Fc chimera was purified from the culture medium using Protein G affinity chromatography.

For MAG binding studies, NG108-15 cells were cultured in the presence of sialic acid precursors for the indicated times, then were released from culture dishes using hypertonic $Ca^{2+}/Mg^{2+}$-free phosphate-buffered saline (Yang et al., *Proc. Natl. Acad. Sci. USA.*, 93:814, 1996) and resuspended (at $2\times10^5$ cells/ml) in 25 mM Hepes-buffered Hanks balanced salt solution (Bashor, *Methods Enzymol.*, 58:119, 1979) containing 5 mg/ml bovine serum albumin. MAG-Fc (6 μg) was added to 100 μl of the same buffer containing 6 μg fluorescein isothiocyanate-labeled goat anti-human Fc (Jackson Immunoresearch, West Grove, Pa.) and incubated on ice for 1 h 45 min with frequent mixing. Cell suspension (100 μl containing 50,000 cells) was added to the premixed antibody solution and the mixture incubated on ice for 45 min. The cells were then centrifuged for 4 sec at 16,000×g and washed three times by resuspension in 200 μl of buffer with bovine serum albumin and centrifugation. The resulting cell pellet was resuspended in 100 μl buffer with bovine serum albumin and flow cytometry was performed on an Epics Profile II cytometer (Coulter Corp, Hialeah, Fla.).

EXAMPLE 2

Cellular Uptake of Sialic Acid Precursors

Figure 3:
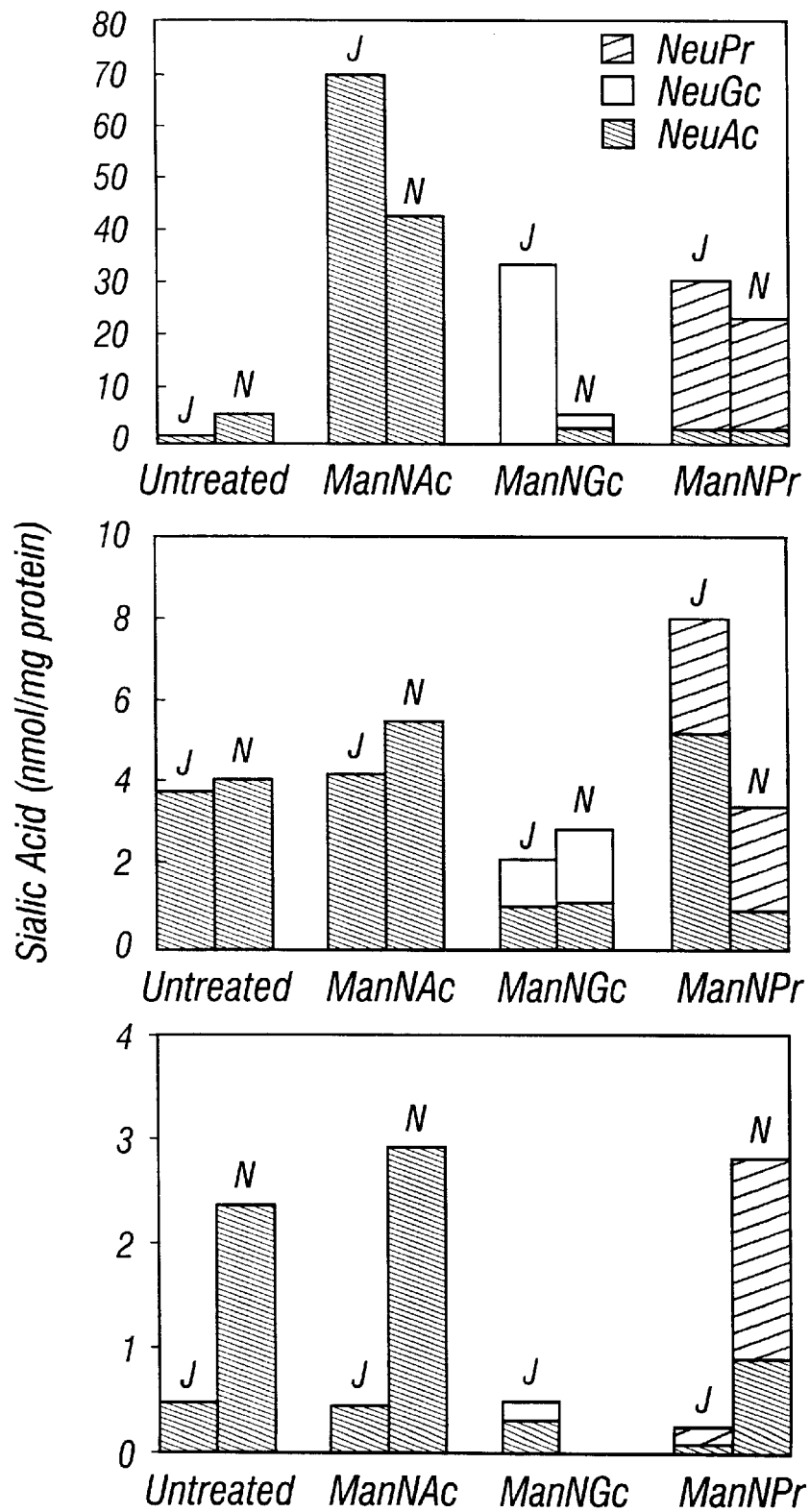
FIG. 3 is a bar graph showing the uptake of N-substituted D-mannosamine derivatives and conversion to sialic acid by NG108-15 and Jurkat cells. NG108-15 (N) and Jurkat (J) cells were treated for 48 hours with the indicated sialic acid precursor (20 mM) and collected.

NeuGc Biosynthesis from ManNGc Monoacetate:

Sialic acid is biosynthesized from the precursor sugar N-acetylmannosamine (FIG. 2). In the present invention, sialic acids are converted on live neuronal cells from NeuAc, which is a key determinant for MAG binding, to NeuGc, which is non-permissive for MAG binding. A potential NeuGc precursor, N-glycolylmannosamine monoacetate (ManNGcMA, FIG. 1, $R_1$=H) was tested for its ability to generate altered sialic acids in neuronal and non-neuronal cells. N-propanoylmannosamine (ManNPr) and other N-acyl mannosamine derivatives have been used to modify glycoprotein associated sialic acids to the corresponding N-acylneuraminic acid. N-propanoyl-mannosamine (ManNPr), was used as a positive control. Jurkat human lymphoma cells and NG108-15 cells (rodent neuroblastoma/glioma hybrid cells) were incubated in 20 mM synthetic precursor or control precursor (N-acetylmannosamine, ManNAc) for 48 h, then harvested. Cell pellets were fractioned into lipid associated, protein associated, and intracellular (lipid and cytoplasmic which may consist of oligosaccharide-bound, free, or CMP-activated sialic acid) sialic acids and hydrolyzed to release sialic acid. The hydrolyzed samples were then analyzed by HPLC to determine sialic acid content. Three fractions were isolated: intracellular and lipid associated sialic acid (A), lipid associated sialic acid alone (B), and protein associated sialic acid (C). The extracts were acid hydrolyzed and analyzed using a Dionex HPLC system with pulsed amperometric detection. Sialic acid is expressed relative to total cellular protein as measured by BCA protein assay of the total protein pellet. Sialic acid precursor pools were quite elastic, in that treatment with 20 mM ManNAc increased intracellular sialic acid as much as 14-fold (FIG. 3, panel A). Similarly, treatment with 20 mM ManNPr resulted in a 4-fold increase in sialic acid, with >95% as N-propanoylneuraminic acid (NeuPr). In contrast, treatment with 20 mM ManNGcMA resulted in a markedly smaller sialic acid precursor pool compared to the untreated control, although most ($\approx$70%) was in the NeuGc form. The differential effect on pool size was cell type or species specific, in that treatment of a human T-cell-related cell line (Jurkat) with 20 mM ManNGcMA resulted in an increase in total sialic acid precursor pool size (comparable to treatment with ManNPr) which was nearly all NeuGc.

Both Jurkat and NG108-15 cells could easily take up and convert the precursors to the corresponding sialic acid derivatives, and high levels of intracellular sialic acid were observed when cells were treated with either N-propanoyl or N-acetylmannosamine (ManNAc). The former resulted in an intracellular sialic acid pool composed predominantly f N-propanolyneuroamic acid (NeuPr, FIG. 3). The presence of the unnatural sialic derivative in ManNPr treated cell extract was confirmed by sensitivity to N-acetylneuraminic acid aldolase. Analysis of cellular glycoconjugates was consistent with previously published data in that N-propanoylmannosamine treatment resulted in $\approx$50% of the glycoprotein associated sialic acid in the form of neuPr for both cell types. Glycolipid associated sialic acid values differed slightly between the two cell types, with Jurkat having 33% and NG108-15 having 70% of their lipid associated sialic acid in the form of N-propanoylneuraminic acid (FIG. 3).

Although ManNPr and ManNGcMA had very different effects on the sialic acid precursor pool size in NG 108-15 cells, the size of the ganglioside pool remained relatively constant (FIG. 3, panel B). Treatment with 20 mM ManNPr converted $\approx$70% of the ganglioside sialic acid to the NeuPr form within 48 h, whereas treatment with 20 mM ManNGcMA resulted in less ($\approx$30%) conversion to the NeuGc form.

The glycoprotein sialic acid concentration was more sensitive to the precursor pool size, with total glycoprotein sialic acid increasing $\approx$2-fold in cells treated with ManNAc, increasing $\approx$1.4-fold in cells treated with ManNPr, and decreasing by $\approx$40% in cells treated with ManNGcMA (FIG. 3, panel C). As with the gangliosides, treatment with 20 mM ManNPr converted $\approx$70% of the glycoprotein sialic acid to the NeuPr form within 48 h, whereas treatment with 20 mM ManNGcMA resulted in $\approx$30% conversion of glycoprotein sialic acids to the NeuGc form.

Figure 6:
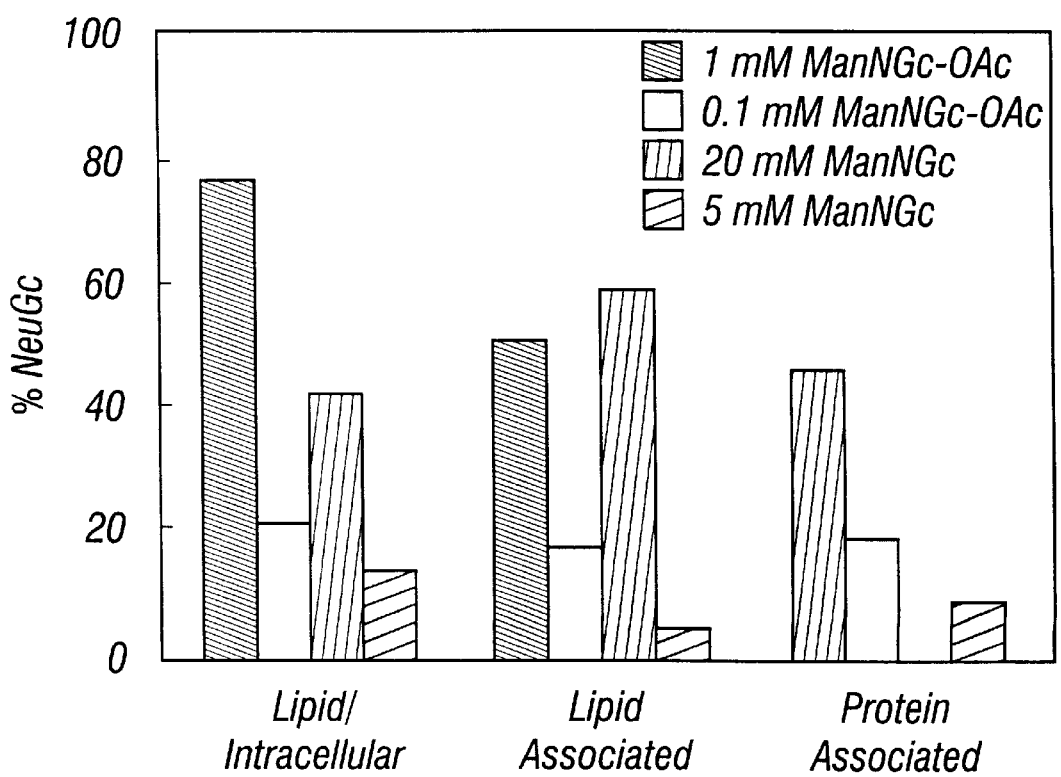
FIG. 6 is a bar graph showing the effect of precursor concentration on uptake and conversion of ManNGc and ManNGc-OAc by NG108-15 cells.

Cells were incubated with the N-glycolylmannosamine percursor for 48 h, and harvested. This resulted in the expected rise in intracellular NeuGc in Jurkat cells, while NG108-15 cells had substantially lower levels. The NeuGc peak was identified by co-migration with standards and sensitivity to the sialic acid specific degradative enzyme, N-acetylneuraminic acid aldolase. The amount of NeuGc on glycoconjugates, however, did not differ substantially from the percentage of NeuPr following N-propanoylmannosamine treatment. Approximately 50% of the protein and lipid sialic acid of Jurkat cells and 70% of the lipid sialic acid in NG108-15 cells were in the form of NeuGc (FIG. 3). Concentrations of 5 mM ManNGc did not result in substantial levels of NeuGc in NG10515 cells in any of the fractions analyzed (FIG. 6).

The decrease in intracellular levels of N-glycolyneuraminic acid in NG108-15 cells could be due either to a differential uptake of ManNGc or rate of conversion to NeuGc as compared to that seen with ManNPr or ManNAc. To determine if the low level of intracellular NeuGc was due to differential uptake, a peracetylated form of N-glycolymannosamine was synthesized (ManNGc-OAc, FIG. 2), as peracetylation of carbohydrates has been shown to significantly increase sugar uptake (FIG. 2, structure 25;26). The structure of the N-glycolylmannosamine peracetate was initially characterized by thin layer chromatography and further confirmed and found to be a 2:1 ratio of alpha to beta anomers by proton NMR.

Although ManNPr was efficiently incorporated into gangliosides and glycoproteins as NeuPr, it was not used to modify MAG binding, since NeuPr is reported to support MAG (Kelm et al., *Eur. J. Biochem.*, 255:663, 1998) whereas NeuGc does not support MAG binding (Collins et al., *J. Biol. Chem.*, 272:1248, 1997).

NeuGc Biosynthesis from ManNGc Pentaacetate.

Figure 4:
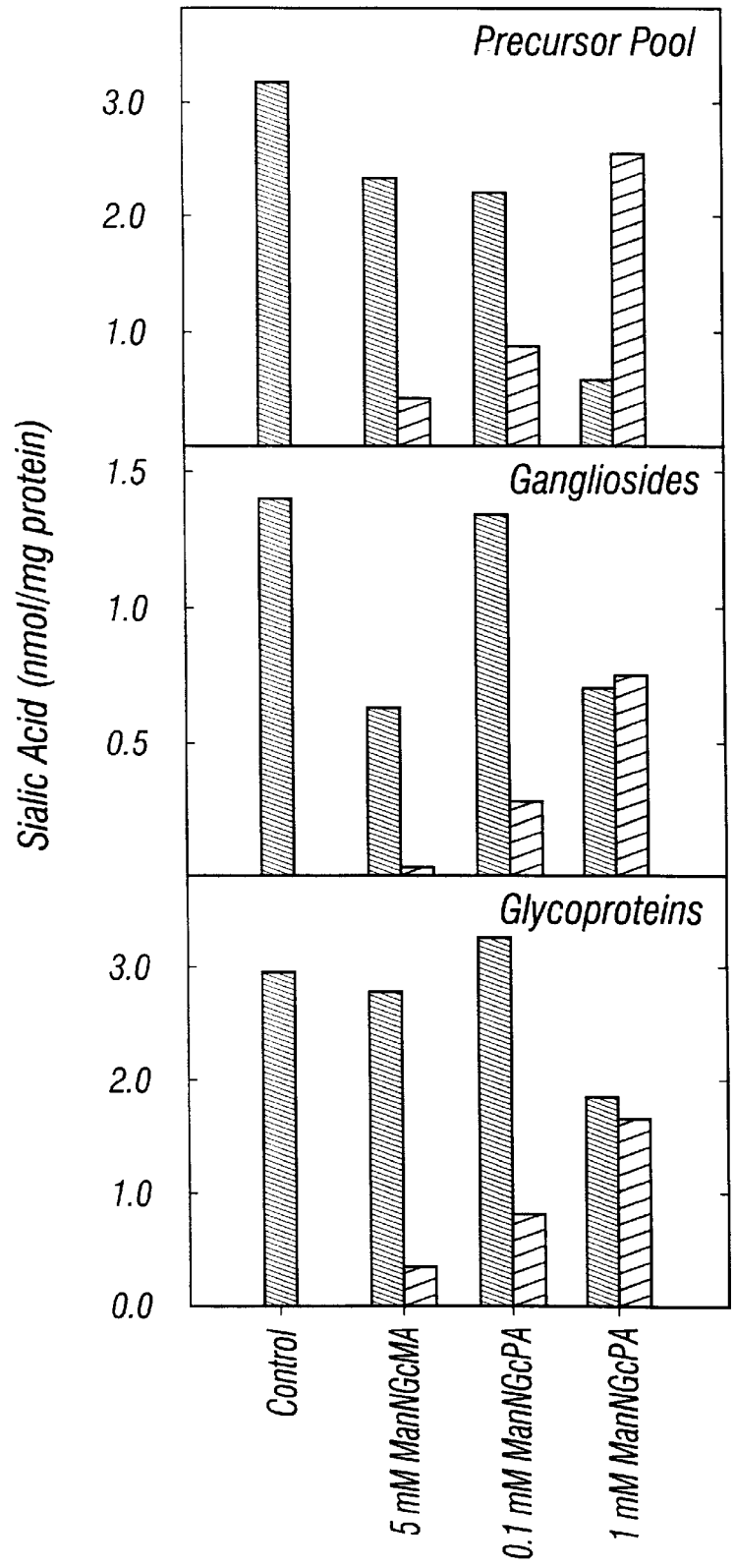
FIG. 4 is a bar graph showing the effect of peracetylation of ManNGc on its conversion to NeuGc and NeuGc-containing sialoglycoconjugates by NG108-15 cells. Sialic acid concentrations (per mg total cell protein) in the intracellular precursor pool, gangliosides, and glycoproteins are shown as indicated. NeuAc, (gray bars); NeuGc, (black bars).

Peracetylation has been shown to greatly increase uptake and anabolic utilization of carbohydrates (Sarkar et al., *J. Biol. Chem.*, 272:25608, 1997). Therefore, ManNGcMA was peracetylated to give N-glycolylmannosamine pentaacetate (ManNGcPA, FIG. 1, $R_1$=Ac) and tested as a precursor for NeuGc biosynthesis. NG 108-15 cells were incubated with 0.1 or 1.0 mM ManNGcPA (or 5 mM ManNGcMA for comparison) for 48 h. Peracetylated sugars were routinely dissolved in dimethylsulfoxide (DMSO), and delivered to the cells in medium containing a final concentration of 0.5% DMSO, which was non-toxic to cells (see below). Whereas none of these treatments significantly altered the sialic acid precursor pool size, treatment with 1 mM ManNGcPA resulted in 82% conversion from NeuAc to NeuGc (FIG. 4, top panel). Treatment with 0.1 mM ManNGcPA resulted in $\approx$2-fold greater conversion to the NeuGc form than did treatment with 5 mM ManNGcMA, indicating an increase in potency of 100-fold due to peracetylation. Incorporation of NeuGc into gangliosides and glycoproteins was related to the precursor pool composition, resulting in $\approx$50% NeuGc within 48 h when cells were treated with 1 mM ManNGcPA (FIG. 4, center and bottom panels) and much less when cells were treated with 5 mM ManNGcMA. Total ganglioside and glycoprotein sialic acid levels were not significantly altered by treatment with the peracetylated precursor.

NG108-15 cells were incubated with the peracetylated compound at 0.1 or 1.0 mM in tissue culture media supplemented with 0.5% DMSO, for 48 hours. Treatment resulted in elevated levels of intracellular sialic acid in the form of NeuGc (FIG. 6; 2.5 to 5 times the intracellular concentration of untreated controls). Non-peracetylated N-glycolylmannosamine at 5 mM in the presence of DMSO, however, did not result in elevated levels of NeuGc. The peracetylated precursor at 1.0 and 0.1 mM resulted in 76.6% and 20.6%, respectively, of the intracellular sialic acid in the form of N-glycolylneuraminic acid while the ManNGc at 5–50-fold higher concentration produced only 13.6% in the form of NeuGc. This difference is also reflected in the incorporation of NeuGc into glycoconjugates.

Glycoproteins contained 47% and 19.8% of their sialic acids as Neugc after treatment with 1.0 and 0.1 mM ManNGc-OAc, respectively. Treatment with 5 mM ManNGc gave only 9.5% of the protein associated sialic acid as NeuGc. Similarly, NeuGc accounted for 51.5%, 17%, and 5% of the total lipid associated sialic acid after treatment with 1.0 mM ManNGc-OAc, 0.1 mM ManNGc-OAc, or 5.0 mM MaNGc, respectively. Although treatment with the peracetyalted compound resulted in substantially elevated levels of intracellular NeuGc, no significant decrease in cell viability, or change in lipid or protein associated sialic acid was observed as compared to DMSO treated control.

Figure 7:
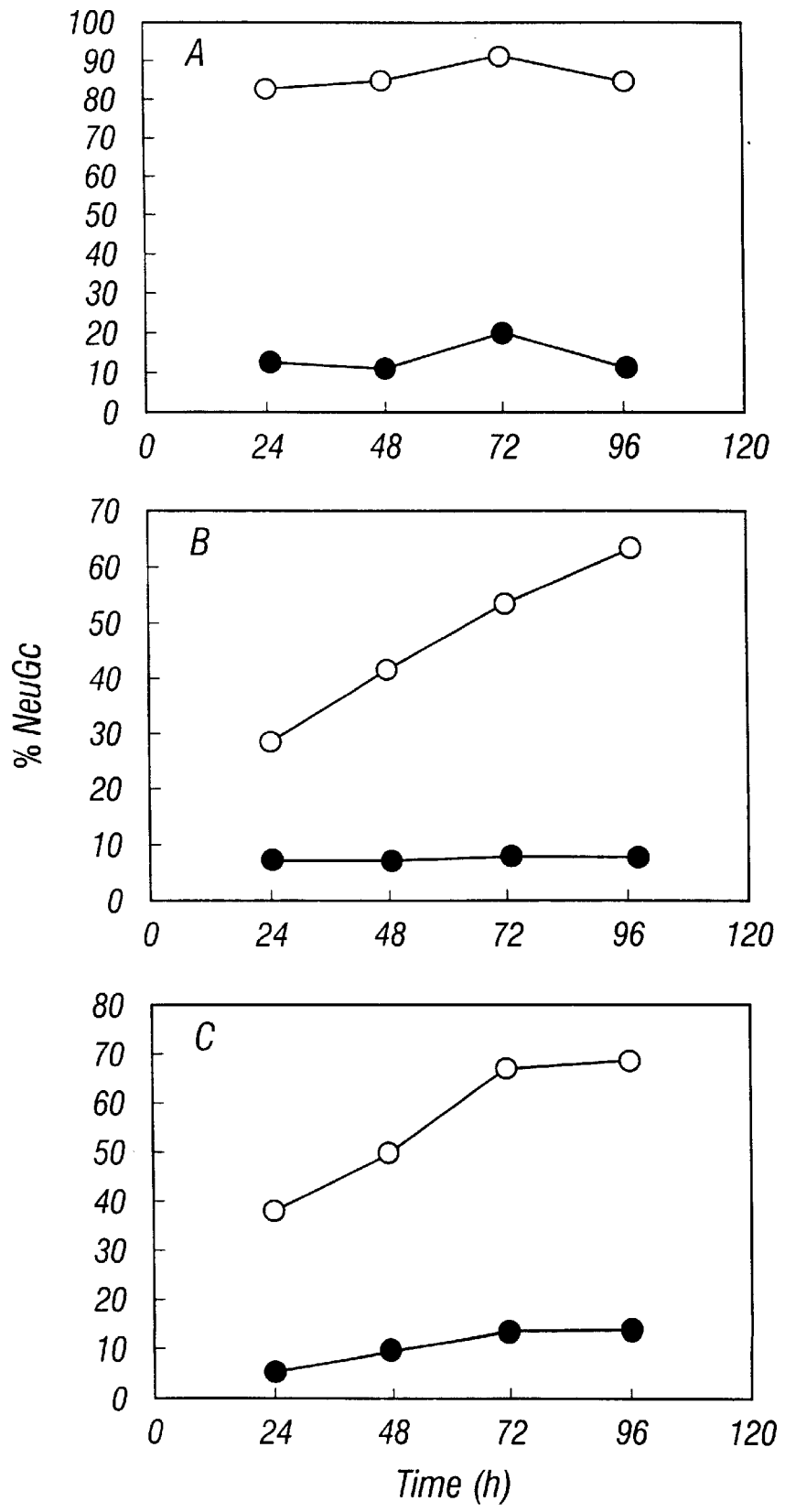
FIG. 7 is a graph of a time course study of ManNGc and ManNGc-OAc metabolism in NG108-15 cells. NG108-15 cells were treated with ManNGc (5 mM) or ManNGc-OAc (1 mM) and collected at 24 hour intervals following treatment. Three fractions were isolated: intracellular and lipid associated sialic acid (A), lipid associated sialic acid alone (B), and protein associated sialic acid (C).

Glycoconjugate associated sialic acid has two potential sources in vivo: Firstly, (I) biosynthesis from N-acetylglucosamine, and (ii) from the recycling of internalized glycoconnugate associated sialic acid. If recycling is a major source of sialic acid for NG108-15 cells, a large intracellular sialic acid pool would be important for increasing derivative expression. This could allow for a favorable competition between the N-acyl derivative and the recycled N-acetylneuraminic acid for the glycoconjugate acceptor. Hence, a longer exposure to the biosynthetic precursor derivative should allow for an increase in glycoconjugate associated NeuGc. To test this, NG108-15 cells were treated with 1 mM ManNGcPA for up to 144 h. The sialic acid precursor pool was >80% in the NeuGc form within 24 h, and remained high throughout the experiment (FIG. 7, top panel). Consistent with prior experiments, half of the ganglioside and glycoprotein sialic acids were converted to the NeuGc form within 48 h. Longer incubation resulted in increased incorporation of NeuGc, with gangliosides expressing ≈80% of their sialic acid as NeuGc and glycoproteins expressing 60–70% as NeuGc as the experiment progressed (FIG. 7, center and bottom panels).

Figure 8:
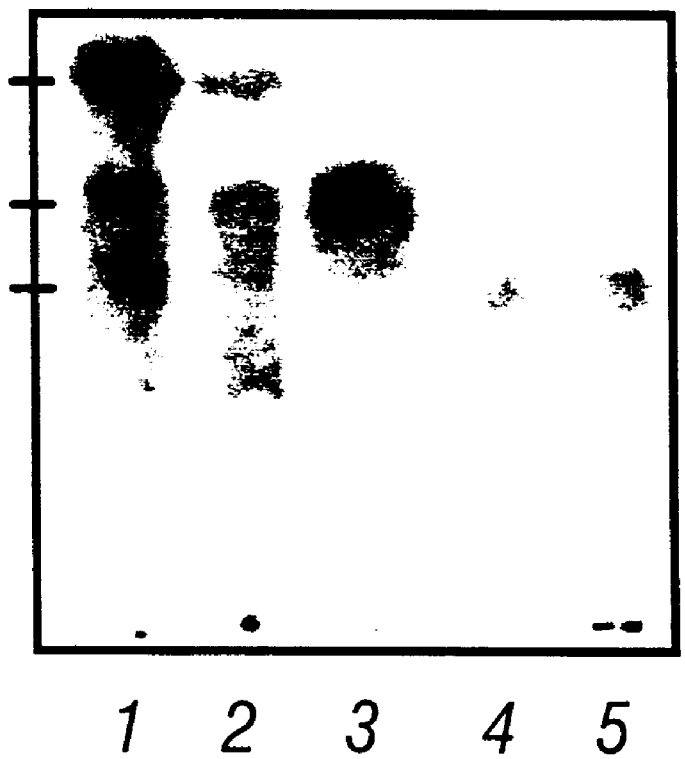
FIG. 8 is a photograph showing the O-Acetylation state of NeuGc in ManNGcPA-treated NG108-15 cells.

To ensure that the per-O-acetylated derivative ManNGcPA did not result in significant production of O-acetylated forms of NeuGc, an aliquot of the extracted polar phase containing free sialic acids from cells treated for 48 h with 1 mM ManNGcPA was subjected to thin layer chromatography in propanol:water (7:3) to resolve O-acetylated from non-acetylated sialic acids. O-Acetylated sialic acids from bovine submaxillary mucin served as standards. The results in FIG. 8 reveal that there is no significant proportion of O-acetylated NeuGc in the precursor pool, confirming apparently complete de-O-acetylation of ManNGcPA prior to or coordinate with its metabolism to sialic acid. A portion of the organic/aqueous soluble pool (predominantly free sialic acids) was subjected to silicic acid thin layer chromatography using propanol-water (1:1) as developing solvent and resorcinol reagent for detection. Sialic acids released from bovine submaxillary mucin, which contain primarily O-acetylated forms of NeuAc (as well as NeuAc, NeuGc, and O-acetylated forms of NeuGc) were prepared and used as positive controls. Lane 1, bovine submaxillary mucin sialic acids; Lane 2, mucin sialic acids pretreated with concentrated ammonium hydroxide for 2 h at ambient temperature to selectively deplete O-acetyl groups; Lane 3, NeuAc standard; Lane 4, NeuGc standard; Lane 5, extract from ManNGcPA-treated NG108-15 cells. O-Acetylated forms of NeuGc, which are reported to migrate 60–100% farther than the parent NeuGc in this system, appear to be absent from the cell extract.

Figure 9A:
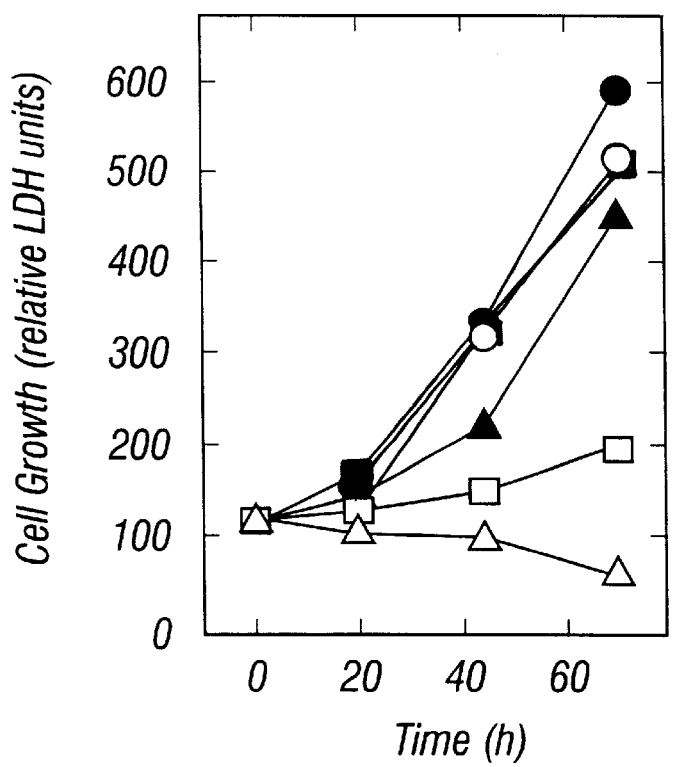
FIG. 9A is a line graph showing the effect of ManNGcPA treatment on NG108-15 cell growth and viability. Cell growth rates were determined in control cultures (■), in cultures treated with 0.08 mM (●), 0.25 mM (○), or 1 mM (□) ManNGcPA, and in cultures treated with 0.25 mM (▲) or 1 mM (△) glucose pentaacetate.
Figure 9B:
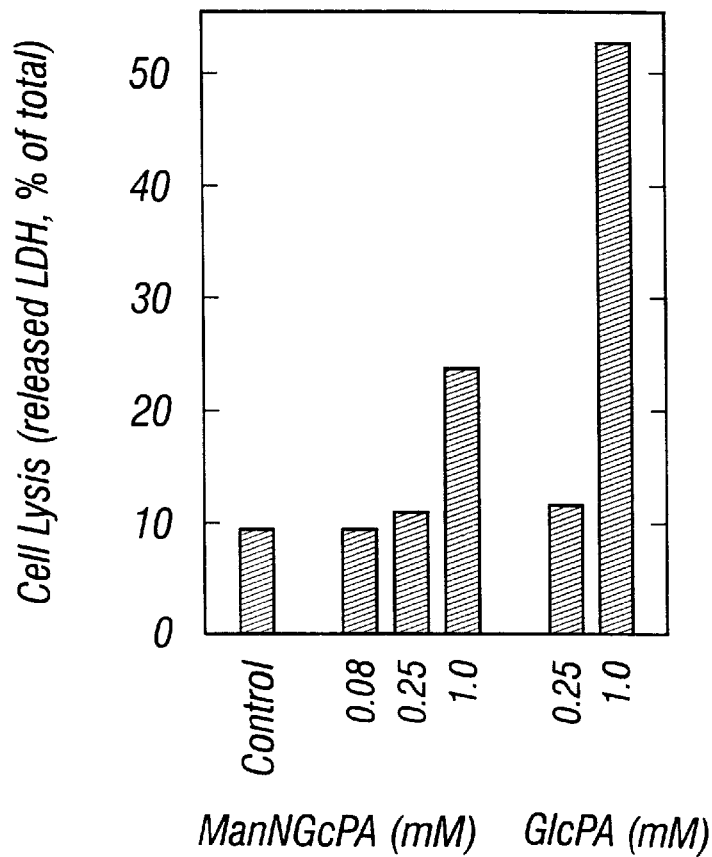
FIG. 9B is a bar graph showing the effect of ManNGcPA treatment on NG108-15 cell growth and viability.

Effects of ManNGcPA-Treatment on Cell Viability and Growth:

Treatment of NG108-15 cells with 1 mM ManNGcPA sharply slowed growth and led to a modest decrease in cell viability after 70 h (from 91% (control) to 76% (1 mM ManNGcPA), see FIGS. 9A and 9B). To address the possible basis for the toxic effects of the precursor, growth and cell viability were compared in cultures treated with glucose pentaacetate as a control. The glucose pentaacetate-treated cells demonstrated more profound decreases in cell growth and viability than the ManNGcPA-treated cells, indicating that uptake and deacetylation of peracetylated precursors, even glucose, is toxic to these cells at 1 mM concentrations. In contrast, treatment with 0.25 mM ManNGcPA resulted in no significant decrease in either cell growth or viability.

Figure 10:
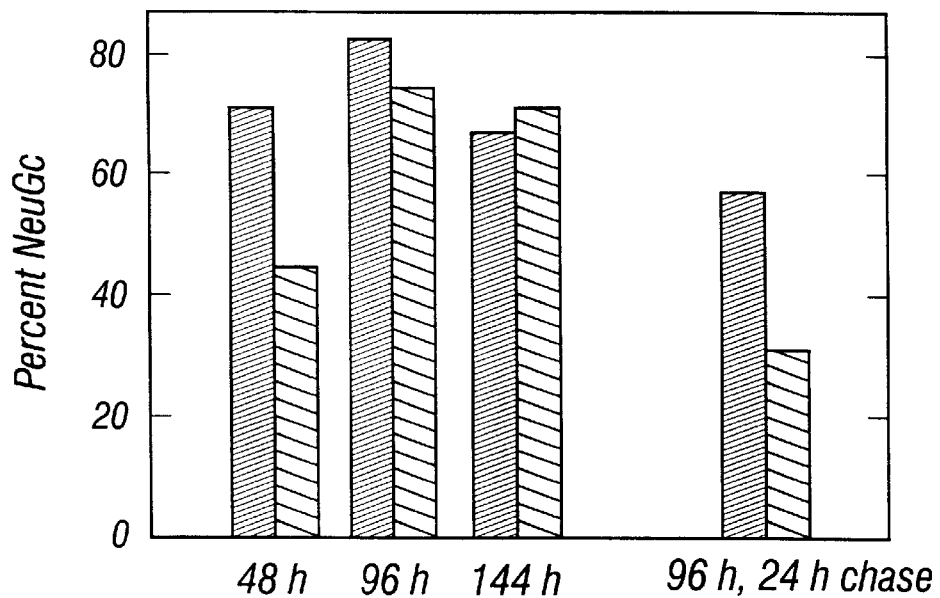
FIG. 10 is a bar graph showing incorporation of NeuGc into glycoconjugates of NG108-15 cells treated with a sub-cytostatic concentration ManNGcPA (0.25 mM). Incorporation of NeuGc into gangliosides (solid bars) and glycoproteins (gray bars) after growth in the presence of 0.25 mM ManNGcPA for the indicated times.

Subsequent kinetic studies revealed that 0.25 mM ManNGcPA treatment resulted in >70% conversion of NeuAc to NeuGc in NG108-15 cell gangliosides after 48 h, and a similar conversion in glycoproteins after 96 h (FIG. 10). Withdrawal of the precursor results in partial reversal of the conversion after 24 h of chase. Growth of the cells in as low as 0.02 mM ManNGcPA for 48 h resulted in nearly 50% conversion of ganglioside sialic acids to the NeuGc form. Incorporation of NeuGc into gangliosides (solid bars) and glycoproteins (gray bars) after growth in the presence of 0.25 mM ManNGcPA for the indicated times was determined. At 96 h one flask of rapidly growing cells was split and equal portions replated in the same medium or in the absence of the precursor (for an additional 24 h) as indicated to determine the rate of reversibility of incorporation. Over the course of the experiment, total ganglioside sialic acid averaged 3.2±0.7 nmol/mg total cell protein (mean±S.D.) and protein sialic acid averaged 3.8±1.2 nmol/mg protein.

Effect of ManNGcPA-Treatment on Myelin-Associated Glycoprotein Binding.

Figure 11:
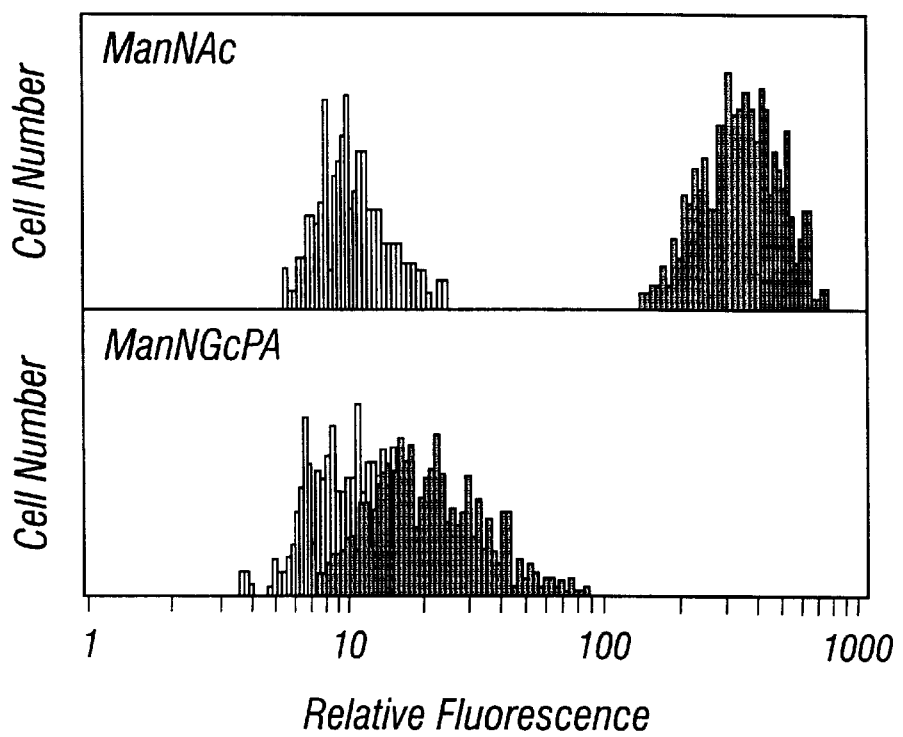
FIG. 11 is a graph showing a flow cytometric analysis of MAG-Fc binding to NG108-15 cells following treatment with 1 mM ManNGc. NG108-15 cells were treated for 144 h with 1 mM ManNGcPA or ManNAc (control). MAG-Fc binding (black bars); secondary antibody only (control) (gray bars).

NG108-15 cells, a mouse neuroblastoma/rat glioma hybrid, display many qualities of cholinergic neurons, including neurite outgrowth, synthesis, storage and release of acetylcholine, and functional synapse formation with muscle cells in vitro. Neurite outgrowth from NG108-15 cells is inhibited by MAG (McKerracher et al., *Neuron*, 13:805, 1994), an interaction which is reversed by pretreatment of the cells with neuraminidase (Schnaar et al., *Ann. N.Y. Acad. Sci.*, 845:92, 1998). To test whether conversion of NG108-15 cell sialic acids from NeuAc to NeuGc results in a loss of MAG binding, cells were treated with 1 mM ManNGcPA for 144 h (at which time 80% of the glycoconjugate sialic acid was in the NeuGc form), collected and incubated with a soluble chimeric protein consisting of the extracellular portion of MAG fused with human Fc as an immunochemical tag. Binding was quantified by flow cytometry. Compared to control cells, specific binding of MAG-Fc to cells treated with 1 mM ManNGcPA was inhibited 95% (FIG. 11). NG 108-15 cells were treated for 144 h with 1 mM ManNGcPA or ManNAc (control). All culture media contained 0.5% (v/v) DMSO. Cells were collected, incubated with MAG-Fc chimera, stained with fluorescent anti-Fc secondary antibody, and subjected to flow cytometry on an Epics Profile II cytometer as described in "Materials and methods." Black bars, MAG-Fc binding; gray bars, secondary antibody only (control).

Figure 12:
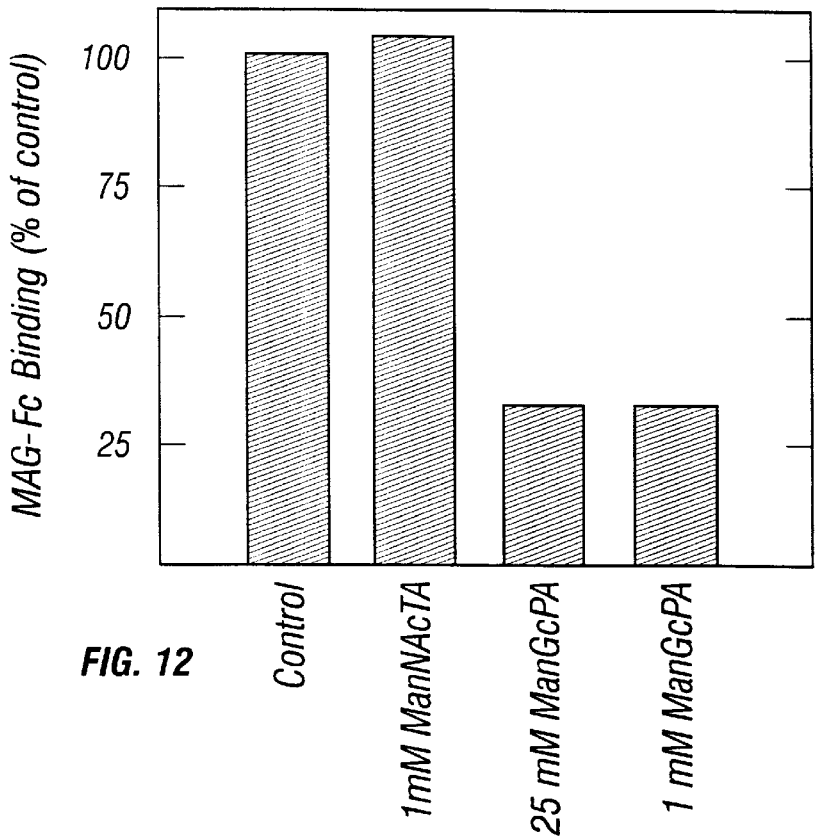
FIG. 12 is a bar graph showing quantification of MAG-Fc binding to NG108-15 cells treated with different sialic acid precursors by flow cytometry.

Treatment with either 0.25 mM or 1 mM ManNGcPA for 96 h (at which time >70% of the glycoconjugate sialic acid was in the NeuGc form) resulted in ≈70% inhibition of MAG-Fc binding, whereas treatment with 1 mM ManNAc-tetraacetate had no significant effect on binding (FIG. 12).

Figure 13:
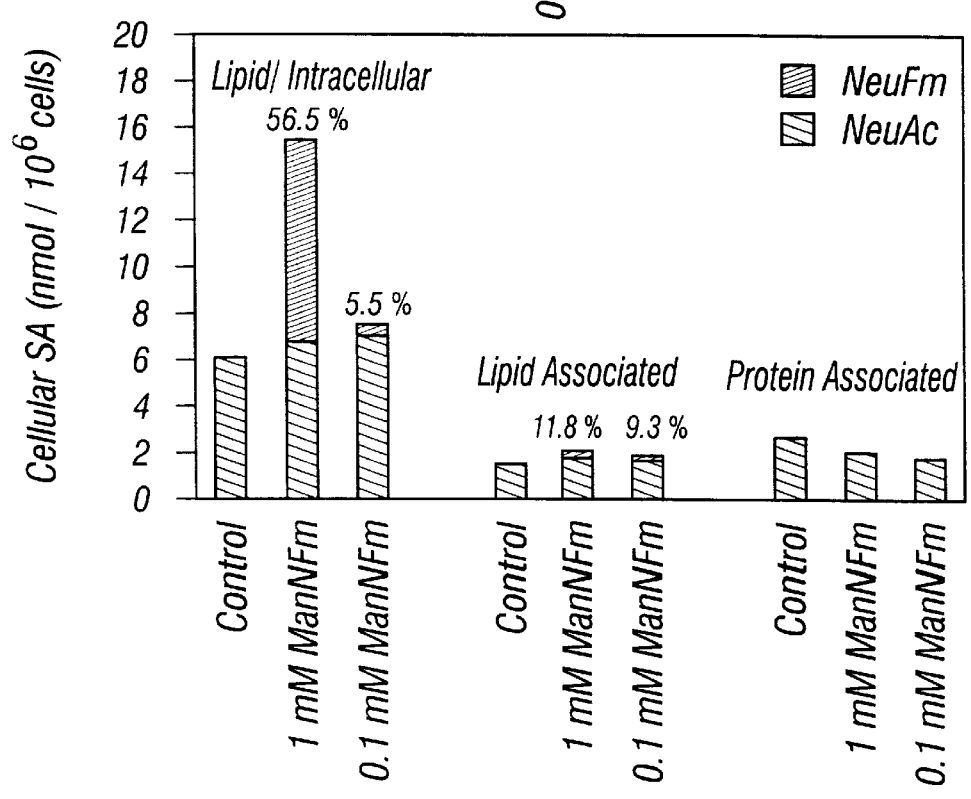
FIG. 13 is a bar graph showing ManNFr-OAc uptake and conversion to NeuFr by NG108-15 cells.

Synthetic N-formyl derivatives of sialic acid have also failed to support MAG recognition. Consequently, the precursor derivative N-formylmannosaminne peracetate (ManNFr-OAc; FIG. 2) was synthesized and incubated with NG108-15 cells. Similar to the results seen with ManNGc-Oac, cells treated with ManFr-OAc had elevated levels of intracellular sialic acid in the form of N-formyneuraminic acid (NeuFr; FIG. 13). NG108-15 cells were cultured for 96 h in medium containing 0.5% DMSO (control) or in the same medium containing the indicated concentrations of ManNGcPA or the peracetylated NeuAc precursor, ManNAc tetra-O-acetate (ManNAcTA). Subsequent transfer onto the nascent oligosaccharide chain of glycoproteins and glycolipids may be slightly slower with this precursor as after 48 hours only 10% of the glycolipid associated sialic acid was as NeuFr. These data show the use of the peracetylated ManNGc and ManNFr in the reengineering of cell surface sialoglycoconjugates.

Sialic acid mass analysis was used to determine, for the first time, absolute levels of incorporation of synthetic and natural N-acylmannosamines into the sialic acid precursor pool, glycolipids (gangliosides) and glycoproteins in the same cell population. Large changes in the precursor pool size did not quantitatively impact sialic acid incorporation into gangliosides, and only modestly affected incorporation into glycoproteins. However, conversion of the precursor pool from exclusively NeuAc to largely NeuPr or NeuGc resulted in incorporation of the modified sialic acids into both gangliosides and sialoglycoproteins. This finding of equivalent incorporation of precursor NeuPr or NeuGc into both gangliosides and sialoglycoproteins in living cells indicates that various sialyltransferases readily use the modified sialic acid precursors.

Both Jurkat and NG108-15 cells were able to convert the N-propanoylmannosamine to the corresponding neuraminic acid efficiently, and this resulted in high levels of intracellular sialic acid similar to that observed with N-acetylmannosamine treatment. The increase levels of sialic acid did not seem to alter cell morphology or viability significantly, and may be important in controlling the amount of N-acyl derivative transferred to glycoconjugates. This intracellular sialic acid fraction is made up of glycolipid associated sialic acid as well as free, oligosaccharide conjugated, and nucleotide activated sialic acid. Although the amount of lipid associated sialic acid is subsequently determined, the remaining intracellular sialic acid composed of free, oligosaccharide conjugated, or CMP-activated sugar is indistinguishable by these methods. Both cell types were also able to transfer a significant amount of the modified sialic acid onto their sialoglycoconjugates, including lipids. The present invention provides the first evidence of incorporation of these precursor derivatives onto glycolipids. Further, peracetylation allowed for elevated levels of intracellular NeuGc with 20 to 50-fold lower concentrations as compared to the non-acetylated ManGc.

N-glycolylneuraminic acid, is extremely rare in humans in any tissue type. Recently, it has been shown that the hydroxylase gene, that is responsible for converting CMP-NeuAc to CMP-NeuAc to CMP-NeuGc, is present in humans, but expresses a nonfunctional truncated mRNA (27). It is likely, then that the transferases responsible for glycoconjugate expression can use both neuraminic acid derivatives as their substrates. This is illustrated in the efficient expression of the N-glycolylneuraminic acid in both the Jurkat (human) and the NG108-15 cells had a low intracellular level of N-glycolylneuraminic acid, both proteins and lipids had significant levels of N-glycolyneuramnic acid.

Myelin-associated glycoprotein is a member of the siglec family of lectins. Its localization to the periaxonal membrane of myelin, directly apposed to the neuronal membrane, made it a likely candidate for neuron-myelin, directly apposed to the neuronal membrane, made it a likely candidate for neuron-myelin communication, and it has subsequently been shown to be involved in the inhibition of neurite outgrowth in the Central Nervous system (CNS). Neurons in the CNS were originally believed to lack the ability to regenerate, like those in the peripheral nervous system, following injury. CNS neurons, however, when not in the presence of CNS myelin, are able to sprout neurites. MAG is one of the myelin components that has been shown to regulate neurite extension. As a lectin, MAG recognizes a sialoglycoconjugate on the neuronal membrane, and removal of neuronal membrane sialic acids allows for neurite extension over a MAG containing myelin extract. Among MAG's requirements for sialic acid recognition is an acetyl group at the 5' position. As there are additional sialic acid lectins in CNS white matter, a more subtle approach for overcoming MAG's inhibition of neurite outgrowth, rather than removal of all neuronal sialic acids, is a desireable tool. Using the ManNGc precursor derivative, the ability for MAG to recognize neuronal cells with converted sialic acid was measured. The 60% decrease in MAG-mediated recognition corresponded directly with the amount (60%) of the glycoconjugate sialic acid in the form of NeuGc.

As with other N-acylmannosamine precursors, treatment with ManNGc (as the monoacetate or pentaacetate) led NG108-15 cells to synthesize and incorporate NeuGc, a major sialic acid found in non-neural tissues of many non-human species. These data outline the synthesis and usage of novel biosynthetic sialic acid precursors that are readily taken up by neuronal and non-neuronal tissues. These precursor derivatives lead to significant modification of the cell glycoconjugate sialic acid profile. Finally, these data outline the potential for these precursors in blocking MAG recognition of neurons and promoting the regrowth of central nervous system neurons.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

It will be apparent to those skilled in the art that various modifications and variations can be made to the compositions and processes of this invention. Thus, it is intended that the present invention cover such modifications and variations, provided they come within the scope of the appended claims and their equivalents.

What is claimed is:

1. A acylated N-mannosamine compound.
2. The compound of claim 1, wherein the mannosamine is acylated at two or more positions.
3. The compound of claim 1, wherein the mannosamine is peracylated.
4. The compound of claim 2, wherein the mannosamine is N-acetylmannosamine.
5. The compound of claim 2, wherein the mannosamine is N-propanoylmannosamine.
6. The compound of claim 2, wherein the mannosamine is N-glycolylmannosamine.

7. The compound of claim 3, wherein the mannosamine is N-glycolylmannosamine peracylate.

8. The compound of claim 3, wherein the mannosamine is N-formylmannosamine peracylate.

9. A method for modulating lectin binding to a cell surface, comprising contacting a cell with the compound of claim 1.

10. The method of claim 9, wherein the cell is a neuronal cell.

11. The method of claim 9, wherein the lectin is myelin-associated glycoprotein (MAG).

12. The method of claim 9, wherein the contacting is in vivo.

13. The method of claim 9, wherein the contacting is ex vivo.

14. A pharmaceutical composition comprising an acylated mannosamine in a pharmaceutically aceptable carrier.

15. The pharmaceutical composition of claim 14, wherein the composition is included in a matrix.

16. The pharmaceutical composition of claim 15, wherein the matrix is a controlled release formulation.

17. The pharmaceutical composition of claim 16, wherein the controlled release formulation is selected from the group consisting of a solid composition, a porous material, a semi-solid, gel or liquid suspension.

18. The pharmaceutical composition of claim 14 in a liposomal form.

19. A method of inhibiting a pathogenic infection in a tissue, comprising contacting the tissue with a composition containing the compound of claim 1.

* * * * *

UNITED STATES PATENT AND TRADEMARK OFFICE
CERTIFICATE OF CORRECTION

PATENT NO.    : 6,274,568 B1
DATED         : August 14, 2001
INVENTOR(S)   : Mr. Brian E. Collins, Ronald L. Schnaar, Mr. Yoshitak Ichikawa, Mr. Thomas J. Fralich It is certified that error appears in the above-identified patent and that said Letters Patent is hereby corrected as shown below:

Column 5,
Line 39, replace "an" with -- a --.

Column 6,
Line 57, delete the first occurrence of "resulting in".

Column 13,
Line 52, delete the first occurrence of "have".

Column 17,
Line 45, delete "aeids" and insert -- acids --.
Line 52, delete ".".

Column 18,
Line 7, delete "C." and insert -- C --.

Column 19,
Line 33, delete "f" and insert -- of --.
Line 39, delete "≈50%" and insert --≅50%--.

Column 24,
Lines 1 and 3, delete "apposed" and insert -- opposed --.

Signed and Sealed this

Twelfth Day of March, 2002

Attest:

*Attesting Officer*

JAMES E. ROGAN
*Director of the United States Patent and Trademark Office*